(12) United States Patent
Mehregany

(10) Patent No.: US 10,565,855 B2
(45) Date of Patent: Feb. 18, 2020

(54) APPARATUS AND METHOD FOR IMPROVED DRUG REGIMEN COMPLIANCE

(71) Applicant: QuantaEd, LLC, San Diego, CA (US)

(72) Inventor: Mehran Mehregany, San Diego, CA (US)

(73) Assignee: QuantaEd, LLC, San Diego, CA (US)

( * ) Notice: Subject to any disclaimer, the term of this patent is extended or adjusted under 35 U.S.C. 154(b) by 0 days.

(21) Appl. No.: 16/179,287

(22) Filed: Nov. 2, 2018

(65) Prior Publication Data
US 2019/0080588 A1 Mar. 14, 2019

Related U.S. Application Data

(63) Continuation of application No. 16/100,430, filed on Aug. 10, 2018, now Pat. No. 10,282,971, which is a
(Continued)

(51) Int. Cl.
*G08B 21/24* (2006.01)
*A61J 7/04* (2006.01)
*A61J 1/03* (2006.01)

(52) U.S. Cl.
CPC .............. *G08B 21/24* (2013.01); *A61J 1/035* (2013.01); *A61J 7/0436* (2015.05); *A61J 7/0481* (2013.01);
(Continued)

(58) Field of Classification Search
CPC ................................. G08B 21/24; A61J 1/035
(Continued)

(56) References Cited

U.S. PATENT DOCUMENTS

| 4,616,316 A | 10/1986 | Hanpeter et al. |
| 4,617,557 A | 10/1986 | Gordon |

(Continued)

FOREIGN PATENT DOCUMENTS

| AU | 2009238236 A1 | 12/2009 |
| WO | 2008/079090 A1 | 7/2008 |

(Continued)

OTHER PUBLICATIONS

Notice of Allowance and Fees Due (PTOL-85) received for U.S. Appl. No. 16/100,430, dated Mar. 13, 2019, 8 pages.
(Continued)

*Primary Examiner* — Qutbuddin Ghulamali
(74) *Attorney, Agent, or Firm* — Kaplan Breyer Schwarz, LLP

(57) ABSTRACT

A method and apparatus for monitoring drug-regimen compliance is disclosed. Systems in accordance with the present invention enable automatic monitoring of the state of medicine content of a blister card. Each tablet location on the blister card is operatively coupled with a different sensor that detects whether the tablet location is occupied and/or a dispensing event at a tablet location. In some embodiments, capacitive sensing is employed, where the capacitance of each sensor is based on the physical state of a dispensing region of the lidding film of the blister pack, which is located at the tablet location being monitored. Alternative sensing approaches are based on optical, acoustic, and tactile sensors that interrogate either the dispensing region at each tablet location or the tablets themselves to determine whether tablets have been dispensed. The sensors interface with a mobile app that provides the user instructions to help improve drug-regimen compliance.

18 Claims, 15 Drawing Sheets

Related U.S. Application Data continuation of application No. 15/223,779, filed on Jul. 29, 2016, now Pat. No. 10,083,594.

(60) Provisional application No. 62/320,234, filed on Apr. 8, 2016.

(52) U.S. Cl.
CPC ........ *A61J 2200/30* (2013.01); *A61J 2205/70* (2013.01)

(58) Field of Classification Search
USPC ...................................................... 340/568.1
See application file for complete search history.

(56) References Cited

U.S. PATENT DOCUMENTS

| | | | |
|---|---|---|---|
| 5,313,439 | A | 5/1994 | Albeck |
| 5,412,372 | A | 5/1995 | Parkhurst et al. |
| 5,852,590 | A | 12/1998 | De La Huerga |
| 6,411,567 | B1 | 6/2002 | Niemiec et al. |
| 7,028,723 | B1 | 4/2006 | Alouani et al. |
| 7,081,807 | B2 | 7/2006 | Lai |
| 7,113,101 | B2 | 9/2006 | Petersen et al. |
| 7,258,005 | B2 | 8/2007 | Nyce |
| 7,630,788 | B1 | 12/2009 | Reese |
| 7,821,404 | B2 | 10/2010 | Walker et al. |
| 7,928,835 | B1 | 4/2011 | Jovanov et al. |
| 8,025,149 | B2 | 9/2011 | Sterry et al. |
| 8,120,492 | B2 | 2/2012 | Scharfeld et al. |
| 8,152,020 | B2 | 4/2012 | Flowers et al. |
| 8,583,281 | B2 | 11/2013 | Bear et al. |
| 8,733,432 | B2 | 5/2014 | Labrecque |
| 8,878,654 | B2 | 11/2014 | Cohen-Alloro et al. |
| 8,960,440 | B1 | 2/2015 | Kronberg |
| 8,963,710 | B2 | 2/2015 | Huang et al. |
| 9,070,063 | B2 | 6/2015 | Carrender |
| 2005/0162979 | A1 | 7/2005 | Ostergaard et al. |
| 2010/0006441 | A1 | 1/2010 | Renaud et al. |
| 2010/0089789 | A1 | 4/2010 | Rosenbaum et al. |
| 2010/0094455 | A1* | 4/2010 | Dehlin .................. A61J 7/0481 700/232 |
| 2012/0024889 | A1 | 2/2012 | Robertson et al. |
| 2012/0056000 | A1* | 3/2012 | Shores .................. A61J 7/0436 235/492 |
| 2013/0085365 | A1 | 4/2013 | Marashdeh et al. |
| 2013/0126379 | A1 | 5/2013 | Medhal et al. |
| 2013/0222135 | A1 | 8/2013 | Stein et al. |
| 2013/0285681 | A1* | 10/2013 | Wilson .................. H05K 1/118 324/693 |
| 2013/0319902 | A1* | 12/2013 | Tufi ........................ A61J 1/035 206/534 |
| 2013/0330684 | A1 | 12/2013 | Dillon et al. |
| 2014/0055267 | A1 | 2/2014 | Rothschild |
| 2014/0118010 | A1 | 5/2014 | Fan et al. |
| 2014/0251850 | A1 | 9/2014 | Huang et al. |
| 2014/0255899 | A1 | 9/2014 | Poullain |
| 2014/0341411 | A1 | 11/2014 | Mohindra et al. |
| 2015/0286852 | A1 | 10/2015 | Sengstaken, Jr. |

FOREIGN PATENT DOCUMENTS

| | | | |
|---|---|---|---|
| WO | 2010/045227 | A1 | 4/2010 |
| WO | 2010/108838 | A1 | 9/2010 |
| WO | 2012/111034 | A1 | 8/2012 |
| WO | 2013/159198 | A1 | 10/2013 |

OTHER PUBLICATIONS

Yongjia (Allen) Yao, "Wearable Sensor Scanner using Electrical Impedance Tomography", Sep. 26, 2012, Publisher: University of Bath, Country: UK.

Yang et al., "A Health-IoT Platform Based on the Integration of Intelligent Packaging, Unobtrusive Bio-Sensor and Intelligent Medicine Box", "Transactions on Industrial Informatics", 2014, pp. 1-13, Publisher: IEEE; DOI: 10.1109/TII.2014.2307795.

Todd O'Connor, "mTouch (TM) Projected Capacitive Touch Screen Sensing Theory of Operation", ISBN:978-1-60932-466-7, Publisher: Microchip Technology Inc., vol. DS93064A, pp. 1-16, Jan. 5, 2010, US.

Silva et al., "Influence of current injection pattern and electric potential measurement strategies in electrical impedance tomography", Mar. 2, 2016, Publisher: Elsevier Ltd., Publication: "Control Engineering Practice", http://dx.doi.org/10.1016/j.conengprac.2016.03.003, Country: BR.

Sarkar et al., "Efficient 2D and 3D electrical impedance tomography using dual reciprocity boundary element techniques", "Engineering Analysis with Boundary Elements", Jul. 1998, Publisher: Research Gate.

Officer: Ioannis Kousouretas, "International Search Report", PCT/US2016/055535, Completed Jan. 16, 2017.

Officer: Jean Sommer, "International Search Report", PCT/US2016/055516, Completed Jan. 5, 2017.

Officer: Hong Djien Ong, "International Search Report and the Written Opinion", International Patent Application No. PCT/US2017/025302, Search Completed Jun. 8, 2017, 12 pp.

Notice of Allowance received for U.S. Appl. No. 15/223,779, dated Aug. 9, 2018, 09 pp.

Non-Final Rejection received for U.S. Appl. No. 16/100,430, dated Jan. 25, 2019, 7 pages.

Non-Final Rejection dated Feb. 8, 2019 for U.S. Appl. No. 16/179,287.

Final Office Action received for U.S. Appl. No. 15/170,121, dated May 29, 2018, 20 pages.

"Non-Final Rejection" issued in US Appl. No. 15/170,121, dated Nov. 20, 2017.

"Final Rejection" issued in related U.S. Appl. No. 14/879,874 dated May 14, 2018.

"Notice of Allowance" issued in related U.S. Appl. No. 15/223,779 dated Apr. 19, 2018.

"Non-Final Rejection" issued in related U.S. Appl. No. 15/223,779, dated Sep. 8, 2017.

"Non-Final Office Action", U.S. Appl. 14/879,874, dated Oct. 10, 2017.

Examiner initiated interview summary (PTOL-413B) received for U.S. Appl. No. 15/170,121, dated Aug. 3, 2018, 1 pages.

Authorized Officer: Melissa Koval, "International Preliminary Report on Patentability" dated Sep. 1, 2017 in PCT Application No. PCT/US16/55516.

Ariel Bogle, "Soon Your Medicine Bottle Could Remind You to Take Your Pills", "Future Tense—The Citizen's Guide to the Future", Aug. 19, 2013, Publisher: ASU I New America I Slate.

Applicant Initiated Interview Summary received for U.S. Appl. No. 15/170,121, dated Jul. 5, 2018, 3 pages.

Applicant Initiated Interview Summary received for U.S. Appl. No. 14/879,874, dated Jul. 5, 2018, 3 pages.

Advisory Action (PTOL-303) received for U.S. Appl. No. 15/170,121, dated Aug. 3, 2018, 4 pages.

Advisory Action (PTOL-303) received for U.S. Appl. No. 14/879,874, dated Aug. 1, 2018, 3 pages.

"The Most Accurate Smart Blister in the World", "med-ic Smart Label", 2011, Publisher: IMC Information Mediary Corp.

"SMRxT Realtime Medication Adherence", 2012-2014, Publisher: SMRxT Inc.; http://smrxl.com/index.php.

* cited by examiner cross-sectional view of region 406

APPARATUS AND METHOD FOR IMPROVED DRUG REGIMEN COMPLIANCE

STATEMENT OF RELATED CASES

This case is a continuation of co-pending U.S. Non-Provisional patent application Ser. No. 16/100,430 filed Aug. 10, 2018, which claims priority to U.S. Non-Provisional patent application Ser. No. 15/223,779 filed Jul. 29, 2016, now U.S. Pat. No. 10,083,594, which claims priority to U.S. Provisional Patent Application Ser. No. 62/320,234 filed on Apr. 8, 2016, each of which is incorporated herein by reference.

BACKGROUND OF THE INVENTION

Medication noncompliance is a costly problem in many ways, from driving up health care costs to financial losses to the pharmaceutical industry to serious negative human impacts:
  125,000 people die in the US each year as a result of failure to adhere to drug regimens;
  Studies reflect $290 billion per year of healthcare implications of medication non-adherence;
  The global pharmaceutical market loses an estimated $564 billion annually, or 59% of the $956 billion in total global pharmaceutical revenue in 2011 due to non-adherence;
  In developed countries, adherence to long-term therapies in the general population is around 50%, and much lower in developing countries; and
  Nearly three out of four Americans are not taking their medications as directed—which results in serious health consequences, especially for people with chronic diseases.

The need to follow a drug regimen properly is particularly acute for oral contraceptive pills (OCP). For example, in addition to the above issues, failure to follow the proper regimen for OCP has already led to countless unwanted pregnancies and could lead to many more. OCP is one of the most popular forms of contraception, particularly among young women. A government report published Oct. 18, 2012 provides the following statistics for the U.S.:
  Sixty-two percent of women of reproductive age are currently using contraception. Of women using a contraceptive method in the month of the interview, the most common methods used are the pill (28%, or 10.6 million women) and female sterilization (27%, or 10.2 million women). Use of intrauterine devices as a current method has increased since 1995 (from 0.8% in 1995 to 5.6% in 2006-2010), whereas fewer women report that their partners are using condoms as their current, most effective contraceptive method. Of women at risk of an unintended pregnancy, 11% report not currently using a method of contraception.

A United Nations report published in 2011 provides the follow statistics worldwide:
  In developed countries as a whole, the most commonly used methods are the pill (used by 18 percent of women of reproductive age who are married or in a union) and the male condom (with 18 percent prevalence). Those two methods accounted for half of all contraceptive use in the developed countries. By contrast, in developing countries the methods with the highest prevalence were female sterilization (21 percent) and the IUD (15 percent), accounting together for 58 percent of overall contraceptive use.

Failure to take a pill is one of the main reasons for seeking emergency contraception (e.g., the morning after pill) in women relying on OCP. A primary cause of unintended pregnancy in these women may therefore be poor adherence. Studies suggest that as much as 47% of women worldwide show poor adherence, missing two or more pills per cycle. (A menstrual cycle is on average 28 days.) Britain's largest manufacturer of OCP, Schering Health Care Ltd, reports that on average women forget to take their pill eight times a year. Most know they have to take remedial steps when they miss a pill, but few know what. Only 10% know missing just one pill places them at risk of pregnancy.

The success of OCP is tightly coupled to adherence to the prescribed daily regimen, i.e., taking the right pill on the right day during a woman's menstrual cycle. For this reason, birth control pills are packaged in blister cards on which a calendar is printed to guide the patient on which pill to take on which day. Furthermore, the recommended intake interval, from day to day, is 24 hours. For this reason, many use daily reminders (e.g., on mobile devices) to help stay compliant. When a patient becomes non-compliant, the manufacturer recommends specific steps to regain compliance and reduce chances of unintended pregnancy in the interim. Unfortunately, the recommended mediation approaches are not always followed correctly, leading to higher risk of unwanted pregnancy.

A packaging approach that provides one or more of improved patient adherence/compliance, treatment results, authentication, and packaging and distribution approaches would be a welcome advance for the pharmaceutical industry and have particular benefit in the realm of OCP regimen compliance, as well as other drug regimens.

SUMMARY OF THE INVENTION

The present invention enables tracking of adherence to drug regimens, such as medicinal prescription regimens, through connected, smart packaging. Embodiments of the present invention are particularly well suited for improving adherence of oral contraceptive pills regimens.

Embodiments of the present invention enable the state of a blister card to be automatically monitored, which enables adherence to a drug regimen to be tracked and/or improved. In some embodiments, the state of the blister card is automatically assessed periodically and compared to its previous state to determine whether a tablet has been dispensed during the intervening period. In some embodiments, the action of dispensing a tablet gives rise to an output signal that enables the dispensing event to be automatically recorded. The history of dispensing events is then compared to a prescribed regiment for the medication contained in the blister card to assess whether the dispensing events have been as prescribed. If an error (i.e., noncompliance) in the dispensing history is detected, an alert is issued to the user, and/or one or more designated persons in the care circle of the user (e.g., caregiver, nurse, doctor, clinic/hospital, parent, partner, relatives, friends, etc.).

Embodiments of the present invention include a package comprising a housing that accepts and locates a blister card containing a plurality of medicine tablets. The package includes a detection module comprising a plurality of sensors that is arranged to match the arrangement of the tablets on the blister card. As a result, each tablet location is operatively coupled with a different sensor. When a tablet is dispensed, its respective sensor is operative for providing an output signal indicating the dispensing event, which enables the dispensing history of the blister card to be compared to the prescribed regimen.

An illustrative embodiment of the present invention is a package comprising a housing that includes a detection module comprising a plurality of capacitive sensors, each of which includes a sense electrode. When the blister card is located in the housing, the blister card and the detection module are operatively coupled such that the lidding foil in the dispensing region of each tablet location and the electrode of its respective sensor collectively define a capacitor whose capacitance is based on the physical state of the dispensing region. A change in this capacitance is indicative that the tablet at that sensor location has been dispensed.

In some embodiments, the detection module includes a plurality of capacitive sensors that are shielded from external noise and interference. In some of these embodiments, the sense electrode is shielded from stray capacitance and electrical noise arising from the other side of the blister card by a drive electrode located between the sense electrode and the dispensing region. The drive and sense electrode are characterized by a mutual capacitance that is affected by fringing fields based on the physical state of their respective dispensing region. In some embodiments, the sense electrode is between a pair of drive electrodes. The drive electrodes shield the sense electrode from stray capacitance and electrical noise received from the top and bottom sides of the blister card/detection module arrangement. In some embodiments, the sense electrode is substantially surrounded, in-plane, by grounded shield lines. As a result, the sense electrode is also shielded from stray capacitance and electrical noise directed at it from the side.

In some embodiments, the package includes a detection module that employs a sensing technique other than capacitive sensing. In some embodiments, the detection module includes optical sensors. In some embodiments, the detection module includes acoustic sensors. In some embodiments, the detection module includes tactile sensors.

In some embodiments, the package is operatively coupled with an accompanying mobile app to help women relying on OCP with good adherence to the prescribed regimen and better management of the efficacy requirements.

An embodiment of the present invention is a system for monitoring the state of a blister card that includes a forming film, a lidding film, and a first tablet contained in a first reservoir defined by the forming film and the lidding film, wherein the system comprises: a housing that is operative for locating the blister card in a first position; a detection module comprising a first sensor, wherein the first sensor is operative for providing a first electrical signal that is based on at least one of (a) the presence of the first tablet in the first reservoir and (b) the physical state of a first dispensing region of the lidding film; and an electronics module that is operative for providing a first output signal based on the first electrical signal.

Another embodiment of the present invention is a system for monitoring the state of a blister card that includes a forming film, a lidding film, and a plurality of tablets that are arranged in a first arrangement, wherein the system comprises: a detection module comprising a plurality of sensors arranged in the first arrangement, wherein each sensor is operative for providing an electrical signal based on the physical state of a different dispensing region of the lidding film; and an electronics module operative for providing an output signal based on the plurality of electrical signals.

Yet another embodiment of the present invention is a method for monitoring the state of a blister card that includes a forming film, a lidding film, and a plurality of tablets that are arranged in a first arrangement, wherein the method comprises: providing a detection module comprising a plurality of sensors that is arranged in the first arrangement; operatively coupling the plurality of sensors and the blister card such that each sensor of the plurality thereof is operative for providing an electrical signal based on the presence of a different tablet of the plurality thereof in the blister card; determining a physical state of the blister card based on the plurality of electrical signals; comparing the physical state of the blister card with an expected state of the blister card, wherein the expected state is based on a predetermined prescription regimen for the plurality of tablets; and providing an output signal based on the physical state of the blister card relative to the expected state.

DETAILED DESCRIPTION

The present invention is directed, in part, to connected-packaging solutions for pharmaceutical products, with a focus on medicine containers comprising blister cards. It should be noted that, although the focus of the instant Specification is on OCP, the present invention can be directed to any blister-card-based packaged product. For the purposes of this Specification, including the appended claims, the term "tablet" is defined to mean any and all variety of medication, which includes, without limitation, pills, capsules, powder, gel-caps, and the like. Some of the embodiments described herein draw on concepts developed for connected packaging solutions directed to "blister cards," which are described in U.S. patent application Ser. No. 14/879,874, entitled "Connected Packaging," which was filed Oct. 9, 2015, and which is incorporated herein by reference.

Figure 1:
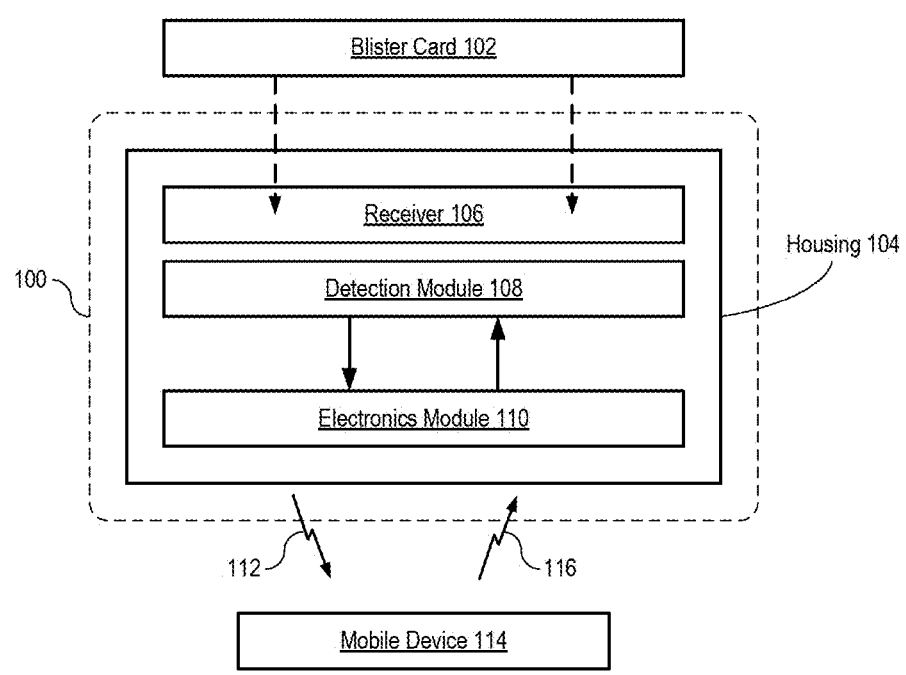
FIG. 1 depicts a block diagram of a package in accordance with an illustrative embodiment of the present invention.

FIG. 1 depicts a block diagram of a package in accordance with an illustrative embodiment of the present invention. Package 100 is an oral-contraceptive protective case that includes smart-packaging capability, which enables it to monitor the state of OCP blister card 102 and enable tracking of the drug regimen for the tablets it contains, initiate messages to the user and/or caregivers, and the like. Package 100 includes housing 104, receiver 106, detection module 108, and electronics module 110. Package 100 is dimensioned and arranged to accept a conventional "push-through-pack" blister card comprising a twenty-eight-day dosage of oral contraceptive tablets and locate the blister card such that it is operatively coupled with the detection module.

Figure 2A:
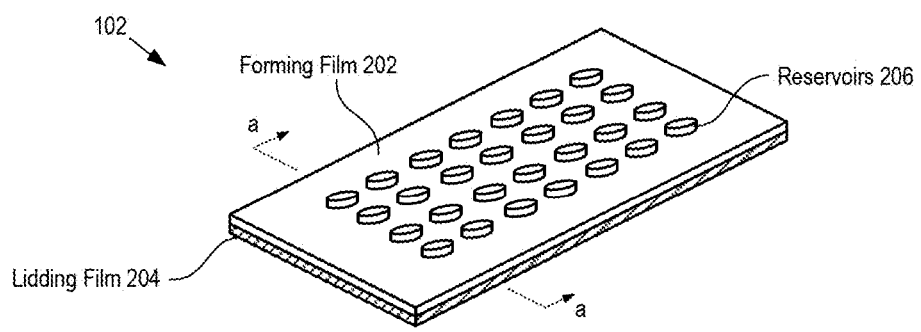
FIGS. 2A-B depict schematic drawings of perspective and cross-sectional views, respectively, of blister card 102.
Figure 2B:
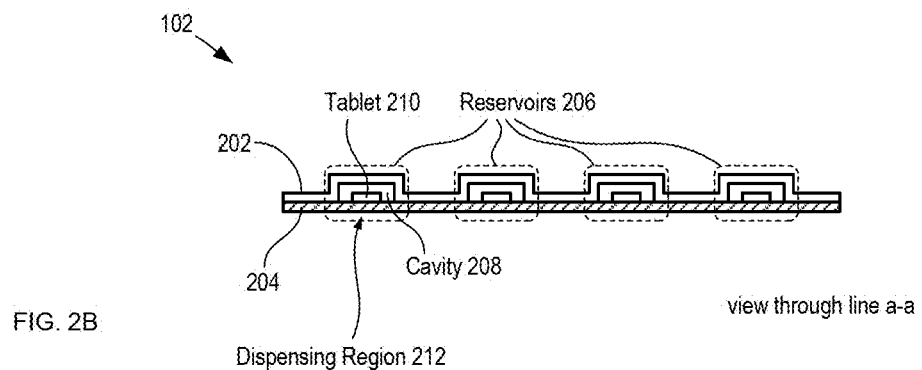

FIGS. 2A-B depict schematic drawings of perspective and cross-sectional views, respectively, of blister card 102. Blister card 102 is a conventional blister card that includes forming film 202, lidding film 204, reservoirs 206, and tablets 210.

Forming film 202 is a layer of thermoformed plastic in which cavities 208 are formed.

Lidding film 204 is a thin sheet of aluminum foil. In some embodiments, lidding film 204 is a sheet of another electrically conductive material. In some embodiments, lidding film 204 includes a sheet of conductive material and a sheet of electrically insulating material, such as a paper sheet (with a printed calendar or instructions), polymer, etc. After tablets 210 are dispensed into cavities 208, lidding film 204 is joined with forming film 202 to seal the cavities, thereby forming reservoirs 206. Typically, a calendar that describes the drug regimen is printed on the card and/or otherwise provided as part of the blister card.

The region of lidding film 204 located under each cavity defines a dispensing region 212, through which its respective tablet 210 is dispensed by pushing the tablet through the lidding foil.

Figure 3:
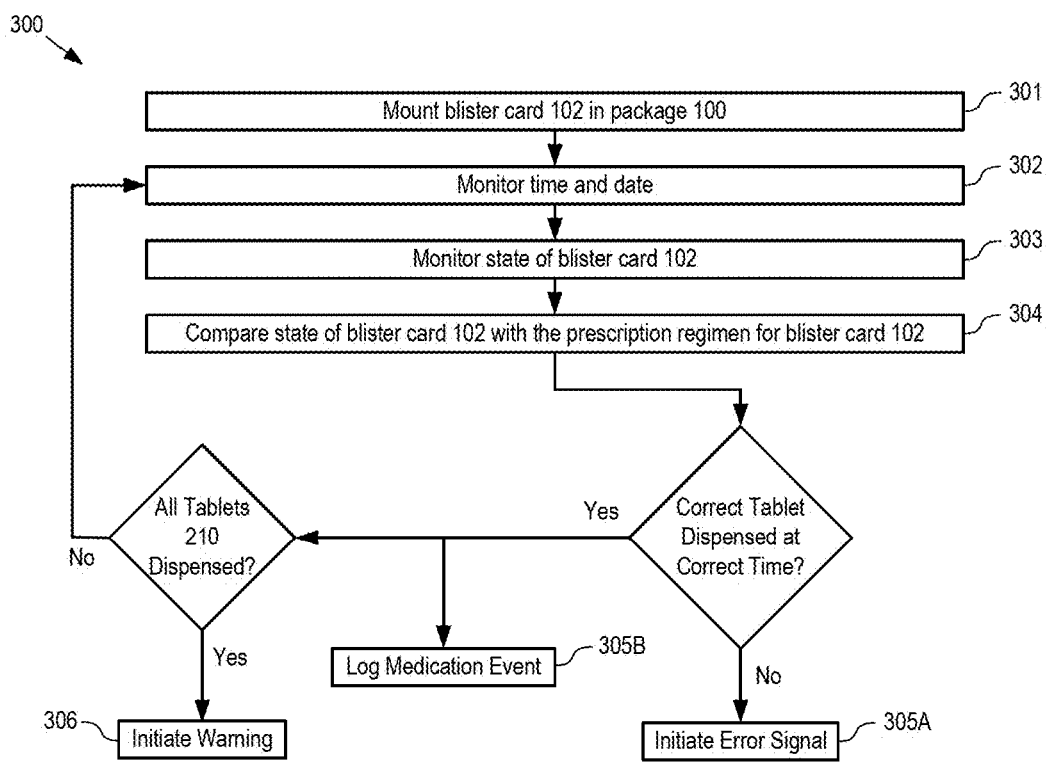
FIG. 3 depicts operations of a method for monitoring a drug regimen in accordance with the illustrative embodiment.

FIG. 3 depicts operations of a method for monitoring a drug regimen in accordance with the illustrative embodiment. Method 300 begins with operation 301, wherein blister card 102 is located in package 100. Method 300 is described with continuing reference to FIGS. 1 and 2A-B.

Figure 4:
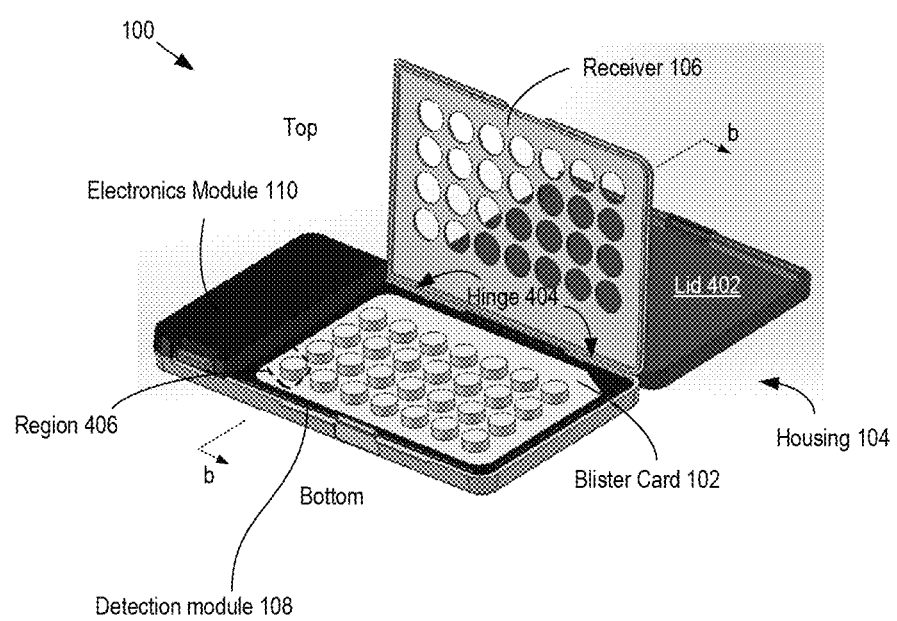
FIG. 4 depicts a schematic drawing of a perspective view of package 100 including inserted blister card 102.

FIG. 4 depicts a schematic drawing of a perspective view of package 100 including inserted blister card 102.

When mounted in package 100, blister card 102 is protected from damage and inadvertent tablet dispensing by housing 104. Housing 104 is an injection-molded plastic case having sufficient strength to protect blister card 102 from damage during normal handling and storage, such as might happen, for example, if blister card 102 were kept in a purse or a pocket without such protection.

The location of blister card 102 within package 100 is determined by receiver 106 (i.e., receiver 106 locates blister card 102). Receiver 106 is a rigid frame containing openings for exposing reservoirs 206 of blister card 102. To locate blister card 102 in housing 104, the blister card is positioned within a seat formed in the bottom of housing 104 (not shown) and receiver 106 is closed over the blister card to trap it in place. Receiver 106 is dimensioned and arranged to provide distributed pressure over the surface of the blister card to ensure that it is operatively coupled with detection module 108.

In some embodiments, blister card 102 includes printed information on its forming-film side (e.g., instructions for the user, advertising, logos, etc.). In such embodiments, those package components (e.g., receiver 106) that overlay such printed information would be made of optically transparent material.

In some embodiments, receiver 106 comprises a different conventional latching system for locating a blister card in housing 104 such that it is operably coupled with detection module 108.

Figure 5:
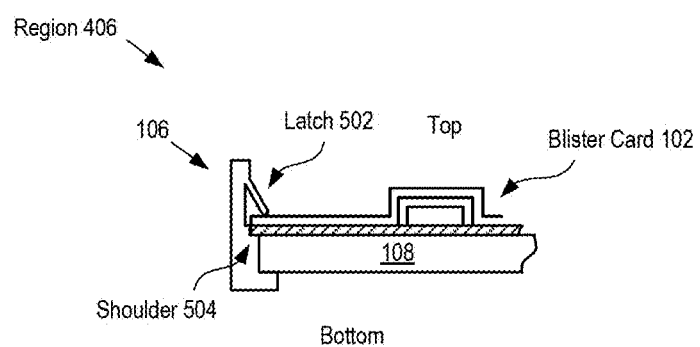
FIG. 5 depicts an enlarged cross-sectional view of a portion of an alternative receiver 106.

FIG. 5 depicts an enlarged cross-sectional view of a portion of an alternative receiver 106. The cross-sectional view depicted in FIG. 5 is taken through region 406 of FIG. 4. Receiver 106 includes a plurality of latches 502 and shoulder 504, which are formed as part of the outer wall of housing 104. Latch 502 is a deformable tab that can be depressed to enable blister card 102 to seat against shoulder 504. The tab is resilient such that once the blister card is located in its proper position against the shoulder, it springs outward to lock the blister card in this position. In the illustrative embodiment, the desired position of blister card 102 is abutting the top surface of detection module 108, as discussed below. Typically, latches 502 and shoulder 504 are formed as part of the sidewalls of housing 104 in accordance with conventional injection molding techniques. One skilled in the art will recognize that there are myriad conventional ways to form receiver 106 and that the receiver designs depicted in FIGS. 4 and 5 are merely examples of receivers suitable for use with the present invention.

Detection module 108 is a two-dimensional arrangement of sensors that substantially matches the arrangement of tablets 210 in blister card 102. In some embodiments, detection module 108 includes a mechanically robust plate comprising a plurality of holes through which tablets 210 are dispensed. As discussed below, detection module 108 employs capacitive sensing technology to monitor the state of blister card 102. It will be clear to one skilled in the art, after reading this Specification, however, that many alternative sensing technologies can be employed in detection module 108 without departing from the scope of the present invention. Sensing technologies suitable for use in embodiments of the present invention include, without limitation, optical sensing, acoustic sensing, and tactile sensing, among others. Detection module 108 is described in more detail below.

Electronics module 110 is an electronics package that is operatively coupled with detection module 108. Electronics module 110 comprises electronic circuitry suitable for interfacing with the sensors of the detection module, signal-conditioning electronics (e.g., pre-amplifiers, comparators, etc.) for receiving the output signals of each sensor, output electronics for providing output signal 112, and the like. In some embodiments, electronics module 110 includes, without limitation:

i. communications electronics (wired and/or wireless, such as Bluetooth, cellular, etc.); or
 ii. processing capability; or
 iii. memory; or
 iv. onboard clock circuitry; or
 v. power (e.g., batteries, etc.) and/or energy scavenging electronics, or
 vi. sensor interface circuitry; or
 vii. wake-up detection circuitry; or
 viii. on-case alerts (e.g., light-emitting diodes, buzzers, etc.); or
 ix. environmental (e.g., temperature, humidity, shock, geolocation, etc.) sensors; or
 x. any combination of i, ii, iii, iv, v, vi, vii, viii, and ix.

In the depicted example, electronics module 110 communicates with mobile device 114 wirelessly via output signal 112 and input signal 116.

Mobile device 114 is a cell phone that runs a software application (i.e., a mobile app) that provides assistance to the patient and/or caregiver to achieve and maintain good adherence to the prescribed drug regimen. In some embodiments, electronics module 110 communicates with a different device, such as a computer and/or base station. Further, in some embodiments, electronics module 110 is integrated with detection module 108 on the same substrate.

In some embodiments, electronics module 110 includes sleep-mode circuitry to facilitate long battery life between charges. In such embodiments, sensing is activated only when desired and the instrument is in sleep mode most of the time. Examples of sleep-mode circuitry suitable for use in embodiments of the present invention include, without limitation, low-power accelerometers, touch/proximity sensors, and the like.

One skilled in the art will recognize, after reading this Specification, that the design features of housing 100 are based on the particular arrangement of blister card 102, as well as the sensing technology used to monitor its state. As a result, the design details provided herein are merely exemplary and that myriad alternative designs are possible without departing from the scope of the present invention.

In the package configuration depicted in FIG. 4, detection module 108 and electronics module 110 are embedded into the bottom surface of housing 104. It should be noted, however, that there are numerous ways to integrate detection module 108 and/or electronics module 110 into housing 104 without departing from the scope of the present invention. In some embodiments of the present invention, for example, detection module 108 is embedded into the bottom of housing 104, while electronics module 110 is mounted on lid 402. Interconnects (not shown) embedded in housing 104 run through hinge 404 to electrically couple the detection and electronics modules. In another embodiment, housing 104 includes an extra compartment to house electronics module 110. In some embodiments, detection module 108 and electronics module 110 are disposed in or on one or more printed circuit boards (PCBs) that are mounted in housing 104 (i.e., a hybrid implementation).

In some embodiments, electronics module 110 includes a touch display disposed on housing 104 to enable direct interaction with the user via displayed text, graphics, user input, and the like.

It should be noted that, although this disclosure provides electronics/sensing/display functionality by locating appropriate electronics, etc., in or on the case, some or all of such functionality can be provided via integration into the blister card itself without departing from the scope of the present invention.

At operation 302, electronics module 110 monitors the time and date via an onboard clock. In some embodiments, mobile device 114 monitors the time and date. In some embodiments, electronics module 110 requests time and date information from mobile device 114. In some embodiments, the time and date is tracked in another conventional manner.

At operation 303, the state of blister card 102 is monitored. One skilled in the art will recognize that the manner in which the state of blister card 102 is determined is based on the sensing technology employed. As mentioned briefly above, many sensing technologies can be used to sense the state of a blister card and examples of several sensing approaches are discussed in detail below.

At operation 304, the state of blister card 102 is compared with the dosing regimen for the prescription it contains (i.e., tablets 210). In the illustrative embodiment, this comparison occurs periodically each day (e.g., every minute, hour, several hours, etc.) throughout the anticipated dosing period of 28 days. In the depicted example, the prescribed dosing regimen is maintained in the mobile app running on mobile device 114, which provides regimen data to electronics module 110 via input signal 116. In some embodiments, the dosing regimen is downloaded into a memory module included in electronics module 110. In some embodiments, output signal 112 provides blister-card-state information to mobile device 114, which compares it to the dosing regimen.

It is an aspect of the present invention that the ability to automatically record dispensing events for a bister card enables improved software, such as mobile apps, for assisting the user to adhere to a prescribed drug regimen. There currently exist numerous cell-phone- and computer-based apps to help OCP adherence through automatic calendar reminders. These apps typically provide features for tracking adherence and some level of management of the efficacy requirements, as well as outline the basic methodology for helping achieve and maintain good adherence and manage the efficacy requirements.

Conventional OCP apps typically begin with a setup stage when the app is first downloaded. The setup step normally requires a user to input several bits of personal information, such as:

Log-in credentials;
 Privacy agreement (Agree or Do Not Agree);
 Cycle Length (only the first time the user launches app);
 First day of last period (only the first time user launches app);
 Number of days since the current card was started (only the first time the user launches); and Daily Reminder settings:
  Time or time window to take a pill;
  Reminder type: alarm, text or email;
  Customized reminder message (e.g., "Take your Pill");
  Snooze activation; and
  Alarm type (e.g., sound).

Once the app is set up, the routine use methodology includes providing reminder alerts to take the correct pill at the correct time (or within the proper time window). After taking a pill, the user then manually enters the time, date, and the pill taken into the app. The time-date-pill data is stored and is accessible to the user to analyze for adherence. The adherence data and trend can also be forwarded to one or more designated persons in the care circle of the user.

The basic limitation of these mobile apps is that the need to manually input all of the necessary data falls to the user, since presently available apps do not have a capability to automatically capture actual adherence data. As a result, prior-art OCP apps are tedious to use, are often incorrectly used, and are most effective only for very motivated patients.

Automated systems for tracking medication adherence via mobile apps are known; however, these are typically directed toward medication packaged in bottles. These conventional systems incorporate wireless connectivity and sensors to monitor and communicate adherence data in an accompanying mobile app and/or network servers. If a dose is missed, the system provides a reminder alert automatically, either by an indicator on the system itself or sent to the care circle of the user via an automated call or text message. The ability to automatically generate a reminder message represents an important step in supporting good adherence.

Embodiments of the present invention include apparatus and methods that enable further improvements to the conventional methodology described above, however. It should be noted that, although these improvements are particularly well suited for OCP compliance, they are also suited for use in many other medication compliance applications as well—particularly those that are significantly affected by the quality of adherence. Specifically, the present invention enables improvements to the prior art due to the fact that it enables:
  monitoring of the distance between the instrument and the mobile device via Bluetooth radio signal range (e.g., up to approximately 20 meters);
  comparisons of actual adherence data from the instruments with OCP manufacturer's instructions stored in a mobile app on the mobile device; and
  provision of adherence-status feedback on the instrument itself, as well as through a mobile app.

As a result, the present invention affords several significant advantages over automated tracking systems of the prior art. For example, the present invention enables an ability to monitor the distance between blister card 102 and a mobile device. This provides monitoring capability that can determine whether the blister card and the mobile device are within the same general space (e.g., a home). As a result, if, for example, the user were leaving her home without her pills, an alert could be sent to the user. The stridency of the reminder could be weighted in importance depending on whether the next dose were due shortly (e.g., in the next hour or the same day) or not until the following day. In some embodiments, information on an electronic calendar kept on the mobile device is accessed to determine the risk in leaving the pills behind, e.g., does she have an overnight trip scheduled, etc.

The ability to compare actual adherence information acquired by package 100 to OCP the regimen for blister card 102 enables embodiments of the present invention to provide a user with next recommended steps. This is particularly advantageous when adherence is interrupted, such as when a pill is missed and the user is unsure of how to best mitigate the risk of an unintended pregnancy.

Further, the present invention enables adherence-status feedback, thereby helping the user to adjust her behavior accordingly. Such feedback also can be provided to the user's care circle for needed intervention toward improving adherence. Still further, in some embodiments, the adherence-status feedback can be stored in long-term memory at a monitoring site for use in long-term care treatment planning, to enable its use as evidence in legal proceedings, civil proceedings (e.g., paternity suits, etc.), and the like.

In some embodiments, the status of the blister card (e.g., number of pills dispensed, which pills have been dispensed, etc.) is saved at case closure. Upon the next opening of the case, the status of the blister card is again examined and compared to the last saved state. This ensures that untimely change of a blister card is detected and the user is asked related questions through the mobile app. Further, the blister-pack state upon opening provides a baseline against which a state change can be measured. In some embodiments, detection of an unanticipated difference between the blister-pack states at closing and opening gives rise to an alarm, error flag, or transmission to the user and/or third party to alert one or both of the possibility of an error.

Returning now to method 300, if operation 304 reveals an improper event, method 300 continues with operation 305A, wherein an error signal is initiated by electronics module 110. Improper events that would initiate an error signal to the user or user's care circle include, without limitation:
  i. the dosing-time window has passed and the anticipated tablet 210 has not been dispensed; or
  ii. an incorrect tablet 210 has been dispensed during the dosing-time window; or
  iii. a tablet 210 has been dispensed at a time other than its proper dosing-time window; or
  iv. more than one tablet 210 has been dispensed; or
  v. any combination of i, ii, iii, and iv.

In addition, in some embodiments, if it has been determined that the time for dispensing a tablet is approaching but the tablet has not been dispensed, a reminder can be sent to the user to encourage her to take the proper pill.

If operation 304 reveals that the correct tablet 210 has been dispensed within its allotted dosing-time window, at operation 305B, the time at which the tablet was dispensed is logged into memory by electronics module 110. In addition, if the tablet dispensed was the last tablet in blister card 102, method 300 continues with operation 306, wherein a warning to the user or user's care circle is initiated to alert them that blister card 102 is now empty. In some embodiments, this warning is generated when the number of tablets in the blister card 102 has dropped to a threshold level so as to initiate a refill reminder to the user or user's care circle, or generate a refill request directly to the pharmacy.

If blister card 102 is not depleted, method 300 continues with the repetition of operations 302 through 306.

The mobile app may incorporate additional features to help the user to better manage her health. For example, at operation 305B, the user may be provided a reward through the mobile and/or an opportunity to input notes into the mobile app, e.g., recording experiencing side effects, having intercourse in the last 24 hours, etc. At operation 305A, the mobile app may provide the user with counseling and education information. Since the point of the cycle for the user is known, the mobile app may provide contextual health and wellness information to the user.

One skilled in the art will recognize, after reading this Specification, that method 300 is merely one non-limiting, exemplary method for improving a drug regimen and that myriad alternative methods can be employed without departing from the scope of the present invention.

Sensing Approaches for Monitoring the State of a Blister Card

As discussed above, many sensing technologies can be exploited for monitoring the state of a blister card, including capacitive sensing, acoustic sensing, optical sensing, thermal, and tactile sensing. Capacitive-sensing technology is particularly attractive for use with the present invention, however. As a result, in the illustrative embodiment, detection module 108 includes a plurality of capacitive sensors, as described herein.

Capacitive Sensing

Figure 6A:
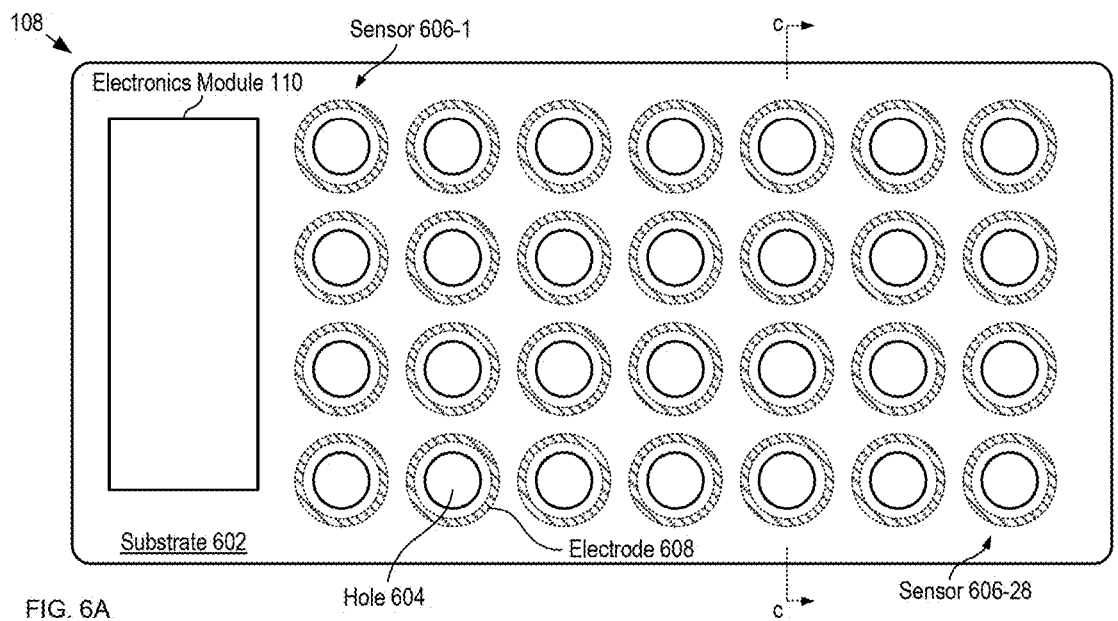
FIGS. 6A-B depict schematic drawings of top and cross-sectional views, respectively, of a capacitive-sensing-based detection module in accordance with the illustrative embodiment of the present invention.
Figure 6B:
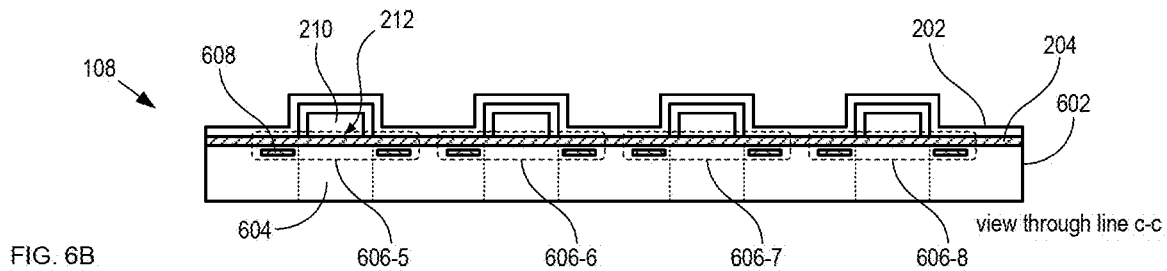

FIGS. 6A-B depict schematic drawings of top and cross-sectional views, respectively, of a capacitive-sensing-based detection module in accordance with the illustrative embodiment of the present invention. Detection module 108 comprises substrate 602, holes 604, and sensors 606-1 through 606-28 (referred to, collectively, as sensors 606).

Substrate 602 is a conventional PCB substrate. Substrate 602 is sized to fit into housing 104 such that it forms the bottom of package 100. Typically substrate 602 is held in housing 104 via a receiver that is analogous to receiver 106 described above. In some embodiments, substrate 602 is another substrate, such as a semiconductor wafer suitable for planar processing, and the like. In some embodiments, instead of a rigid substrate (e.g., substrate 602), detection module 108 comprises a substrate that is flexible and optionally visually transparent, as discussed below and with respect to FIGS. 13A-B.

Holes 604 extend through substrate 602 to allow for the passage of each of tablets 210 through detection module 108 when they are dispensed from the blister card.

Each of sensors 606 includes an electrode 608 and its respective dispensing region 212 of lidding film 204. Electrode 608 is a planar, circular metal electrode that completely surrounds hole 604. Electrode 608 is formed within the body of substrate 602 such that, when blister card 102 is in contact with detection module 108, the electrode and lidding film 204 form a capacitive sensor 606, whose capacitance is based on the state of the lidding film in its respective dispensing region 212, as depicted in FIG. 6B. In some embodiments, sensors 606 (as well as other sensors described herein) are formed directly on a surface of the bottom of housing 104, thereby obviating substrate 602.

Each of sensors 606 is electrically connected to sensing circuitry in electronics module 110 via electrical traces (not shown for clarity). As a result, each sensor can be monitored individually to enable specificity of the dispensing of each tablet 210 of blister card 102. In some embodiments, sensors 606 are electrically connected and interrogated using a row/column addressing scheme.

OCP represents one of many applications wherein it is critical to be able to identify when a tablet has been dispensed during a dispensing event. One skilled in the art will recognize, however, after reading this Specification, that not all medication requires the ability to uniquely identify the identity of a tablet that has been dispensed and, as a result, the sensing approach used to detect tablet dispensing can be greatly simplified. For example, in some cases, all of the tablets of a blister card are substantially identical. In some embodiments of the present invention, therefore, all of sensors 606 are electrically connected in parallel or serially and specificity for which tablet 210 is dispensed is not enabled. In some such embodiments, a single sensor is used to detect dispensing events, such as an accelerometer operatively coupled with the blister card, a single capacitive sensor that spans all the tablet sites such that each dispensing event is indicated by a change in the capacitance of this solitary capacitor.

Alternatively, in some embodiments, row/column sensing is simplified to row or column sensing wherein, for example, one electrode of a capacitive sensor is common to an entire row or column of tablet locations, while the other electrode is divided into site-specific individual electrodes.

In such embodiments, exhaustion of a blister card (which denotes a refill is due) can be detected in numerous ways, such as simply tracking the dispensing events and comparing their count to the total count of the tablets on the blister card as provided or monitoring of the total magnitude of the sensor output signal change with dispensing events and comparing the result with a reference magnitude change determined, for example, by prior calibration operation.

In each sensor 606, the conductive material (i.e., lidding film 204) of its dispensing region 212 forms fringing fields with its electrode 608. These fringing fields impact the capacitance of the capacitive sensor giving it a first value when the dispensing region is intact. When tablet 210 is dispensed, however, the breakage of dispensing region 212 changes the physical configuration between the lidding film material and electrode 608, which affects the fringing fields and, therefore, the capacitance of sensor 606. It should be noted that the capacitance of sensor 606 changes whether or not the material of dispensing region 212 breaks away entirely or pieces of it remain hanging in hole 604 thereafter.

To sense the capacitance of each sensor 606, lidding film 204 is electrically grounded, while each electrode 608 is connected to a high-impedance sense circuit. In some embodiments, lidding film 204 is left electrically "floating;" however, grounding the lidding film is preferable because it provides improved sense-signal stability and noise immunity. Unfortunately, sensor 606 can be sensitive to external noise and interference, such as stray or parasitic capacitances, electromagnetic interference (EMI), and the like.

In some embodiments, in order to mitigate the effects of noise and interference, electrode 608 is segmented into a pair of half-rings. In some embodiments, electrode 608 is segmented into more than two circumferential sections. Using such electrode configurations, capacitive sensing is implemented by monitoring the change in the capacitance between the electrode segments, which is still affected by fringing fields between the electrode segments and the aluminum foil over the hole. Unfortunately, while segmenting electrode 608 provides some measure of noise immunity, noise and interferences can still be a problem.

Figure 7:
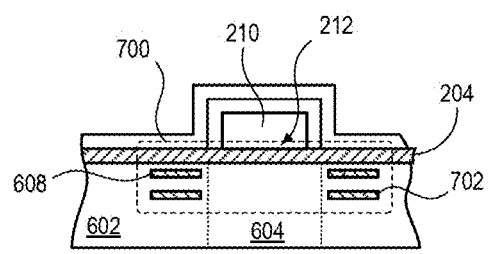
FIG. 7 depicts a cross-sectional view of an alternative capacitive sensor having improved noise immunity in accordance with the present invention.

FIG. 7 depicts a cross-sectional view of an alternative capacitive sensor having improved noise immunity in accordance with the present invention. Sensor 700 is suitable for use in detection module 108 and comprises substrate 602, electrode 608, and electrode 702. Sensor 700 has significantly improved noise immunity as compared to sensor 606.

Electrode 702 is analogous to electrode 608; however, electrode 702 is formed within substrate 602 such that it is parallel with electrode 608 and located distal to lidding film 204 when blister card 102 is located in package 100. Electrodes 608 and 702 collectively define a parallel-plate capacitor within substrate 602.

Sensor 700 operates in accordance with projected capacitive sensing techniques, such as those described in Microchip Application Note TB3064 entitled, "mTouch™ Projected Capacitive Touch Screen Sensing Theory of Operation," published Jan. 5, 2010, which is incorporated herein by reference.

Figure 8:
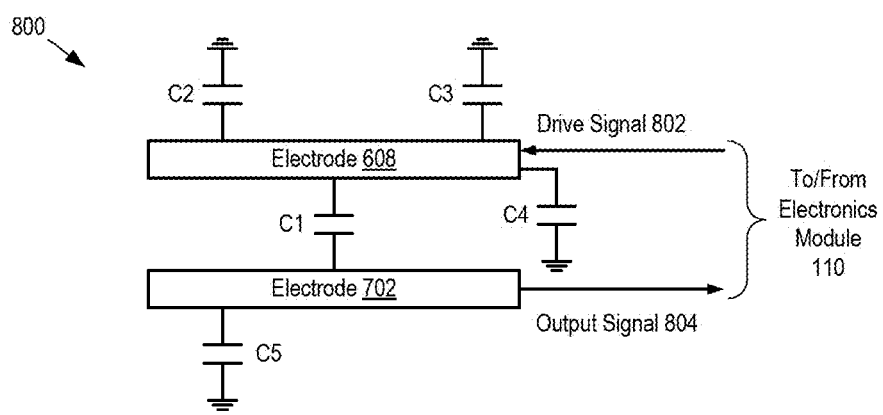
FIG. 8 depicts a schematic drawing of the electrical connectivity of sensor 700.

FIG. 8 depicts a schematic drawing of the electrical connectivity of sensor 700.

In circuit 800, electrodes 608 and 702 collectively define capacitor C1, whose value is determined by the mutual capacitance between the electrodes.

Electrode 608 and lidding film 204 collectively define capacitor C2, whose capacitance is determined by the fringing fields between electrode 608 and the lidding film. These fringing fields are based on the state of detection region 212.

Capacitance C3 is the touch capacitance between electrode 608 and the finger of the user, which develops only while the user is pressing on forming film 202 to push tablet 210 through lidding film 204 and after the lidding film has broken in dispensing region 212, as discussed below.

Electrode 608 is also characterized by substantially fixed electrode capacitance C4.

In similar fashion, electrode 702 is characterized by its own substantially fixed electrode capacitance C5.

In operation, electrode 608 is driven as a transmitter and receives drive signal 802 from electronics module 110. Electrode 702 operates as a receiver and provides output signal 804 to sensing circuitry in electronics module 110, where the output signal is based on mutual capacitance C1.

Prior to the dispensing of tablet 210, detection region 212 is whole and fringing capacitance C2 and mutual capacitance C1 are substantially unchanging since the physical configuration of their respective elements remains fixed. In addition, the value of capacitor C3 is substantially zero, since the intact lidding film 204 in the detection region 212 shields electrode 608 from stray capacitance and electrical noise from regions opposite lidding film 204 from the electrodes. In other words, the intact lidding film 204 in the detection region 212 acts as an "electrical shield" for electrode 608. For the purposes of this Specification, including the appended claims, an "electrical shield" is defined as an element that mitigates the effects of stray capacitance, electrical noise, and electrical interference on an electrical parameter measured at another element.

When tablet 210 is dispensed, however, detection region 212 is broken, which changes the physical configuration between the conductive material of lidding film 204 and electrode 608 and, therefore, the fringing capacitance of capacitor C2. It also enables the capacitance of capacitor C3 to develop. The change in the configuration of the elements of C2 affects mutual capacitance C1. Since the shielding capability of lidding film 204 is compromised by its breakage in dispensing region 212, the value of C1 is further affected by the development of touch capacitance C3. The resultant change in C1 is then detected by the sensing circuitry of electronics module 110.

Unfortunately, while an improvement over the noise immunity of sensor 606, in sensor 700, high-impedance electrode 702 remains unshielded for noise and interference received from directions other than from the top of housing 104.

Figure 9:
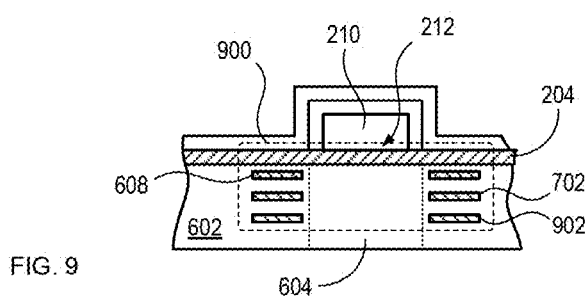
FIG. 9 depicts a cross-sectional view of another alternative capacitive sensor having improved noise immunity in accordance with the present invention.

FIG. 9 depicts a cross-sectional view of another alternative capacitive sensor having improved noise immunity in accordance with the present invention. Sensor 900 is suitable for use in detection module 108 and comprises substrate 602, electrodes 608 and 702, and electrode 902. Sensor 900 has significantly improved noise immunity as compared to sensors 606 and 700.

Electrode 902 is analogous to electrode 702; however, electrode 902 is formed within substrate 602 such that it is parallel with electrodes 608 and electrode 702 but located such that electrode 702 is between electrodes 608 and 902. Electrodes 608 and 702 collectively define a first parallel-plate capacitor within substrate 602 and electrodes 702 and 902 collectively define a second parallel-plate capacitor with the substrate.

Figure 10:
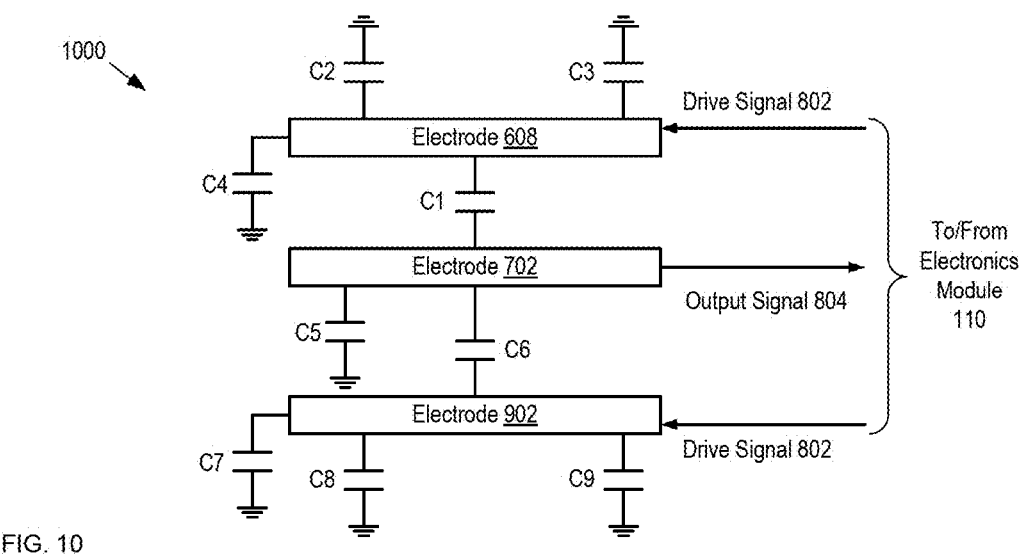
FIG. 10 depicts a schematic drawing of the electrical connectivity of sensor 900.

FIG. 10 depicts a schematic drawing of the electrical connectivity of sensor 900. In circuit 1000, electrode 702 operates as a sense electrode that is sandwiched between driving electrodes 608 and 902, which shield the sense electrode from noise and interference emanating from above blister card 102 and below housing 104.

Electrodes 702 and 902 collectively define capacitor C6, whose value is determined by the mutual capacitance between these electrodes.

Electrode 902 and lidding film 204 collectively define capacitor C7, whose capacitance is determined by the physical configuration between electrode 902 and lidding film 204. Like capacitor C2, the value of this capacitance is based on the state of detection region 212.

Electrode 902 is also characterized by capacitor C8, which is analogous to capacitor C3, described above.

Electrode 902 is also characterized by substantially fixed electrode capacitance C9.

The operation of sensor 900 is analogous to that of sensor 700; however, the fringing-field capacitances of sensor 900 additionally include C1 and C8, whose capacitances are determined by the fringing fields between electrode 902 and lidding film 204, as well as touch capacitances C3 and C8. As in sensor 700, the values of fringing-field capacitances C7 and C8 are based on the state of detection region 212, although the value of C7 can also be influenced by the touch of the user on the back of housing 104.

In some embodiments, additional shielding is provided for sense electrodes 702 by adding shielding lines that surround each sense electrode in its plane within substrate 602.

Figure 11:
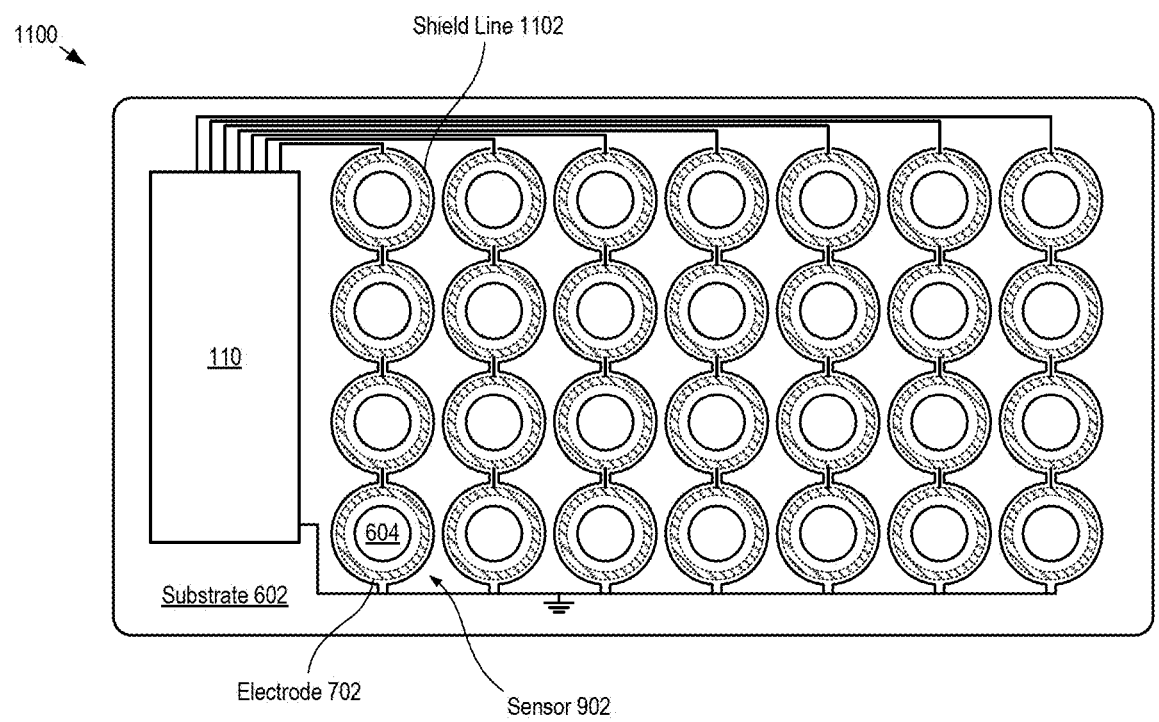
FIG. 11 depicts a plan view of a detection module having improved noise immunity by virtue of shield lines formed around each of its sense electrodes.

FIG. 11 depicts a plan view of a detection module having improved noise immunity by virtue of shield lines formed around each of its sense electrodes. Detection module 1100 is analogous to detection module 108; however, detection module 1100 includes a plurality of sensors 900 and shield lines 1102. FIG. 11 depicts a section of detection module 1100 as taken through the plane of electrodes 702.

Shield lines 1102 are electrically conductive traces formed such that they nearly completely encircle sense electrodes 702 in the plane of the electrodes. Shield lines 1102 are electrically grounded as depicted in the figure.

By virtue of the shielding provided by electrodes 608 and 902 and shield lines 1102, each of sense electrodes 702 is virtually completely shielded from interference from all external noise and EMI sources. It should be noted that shield lines 1102 can also be incorporated into sensors 606 and 700, described above.

It should be noted that, in the depicted example, electrodes 702 are optionally electrically connected together in each column of the 7×4 array of sensors 900. Even though they are electrically connected as shown, each sensor 900 can be individually detected by employing a row-column addressing scheme in which each row of drive electrodes 608 and 902 are driven in either a time-division-multiplexed fashion, or with different drive frequencies. In some embodiments, each of electrodes 702 is individually electrically connected with electronics module 110.

Figure 12A:
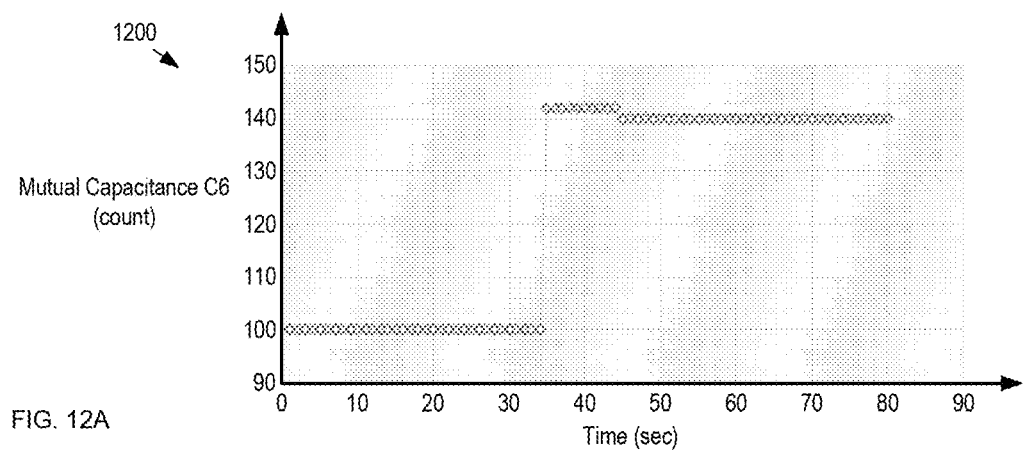
FIGS. 12A-B depict measurement results for two individual sensors 900 in response to the sequential dispensing of two tablets from blister card 102.
Figure 12B:
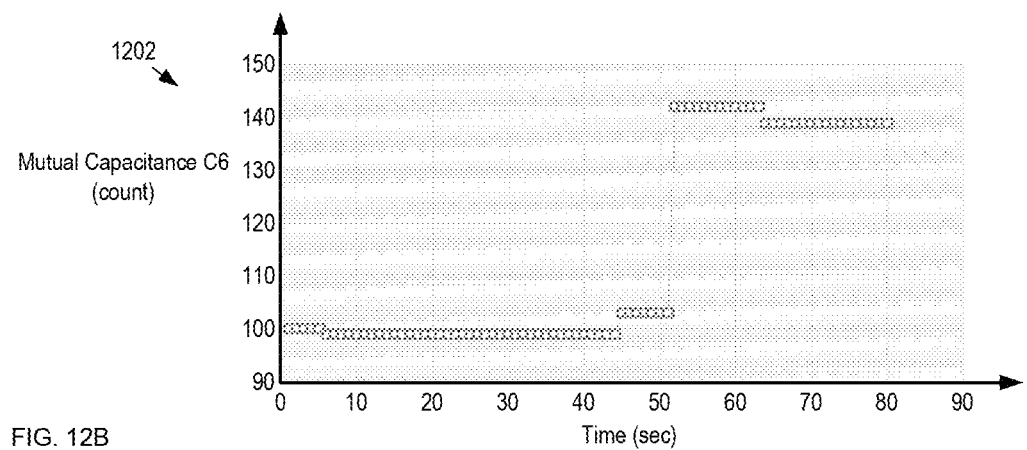

FIGS. 12A-B depict measurement results for two individual sensors 900 in response to the sequential dispensing of two tablets from blister card 102. Plots 1200 and 1202 show the capacitance of mutual capacitor C6 versus time for two sensors 900 in detection module 1100. In plot 1200, tablet 210 is dispensed at a time of 34 seconds. In plot 1202, tablet 210 is dispensed at a time of 45 seconds. As plots 1200 and 1202 show, for each sensor, the corresponding mutual capacitance changes significantly, enabling detection of each dispensing event. It should be noted that the presence or absence of a tablet 210 in each reservoir 206 can also be determined by the absolute magnitude of these sense capacitances, using a previously calibrated threshold value to indicate presence or absence of a tablet in each reservoir 206.

It should be further noted that the sensing principle might also be changed in the implementation of the instrument. In previously filed U.S. patent application Ser. No. 14/879,874, filed on Oct. 9, 2015, and U.S. patent application Ser. No. 15/170,121, filed Jun. 1, 2016, each of which is incorporated herein by reference, the use of electrical impedance tomography (EIT) and electrical capacitance tomography (ECT) to image the state of a blister card (i.e., which pill locations are dispensed and which are intact) and detect dispensing events are disclosed. In some embodiments, the apparatus and methods described therein are employed in the present invention to enable imaging of the state of the OCP card and detect dispensing events.

Still further, in some embodiments, predictive models/algorithms based on modeling and experimentation are used to relate specific sensor output signatures with dispensing events. The model is then used for tablet identification during a dispensing event based on the sensor output. For example, the output signatures of a motion sensor in a detection module would enable the location at which a dispensing event occurred to be determined by utilizing a respective predictive model/algorithm.

Figure 13A:
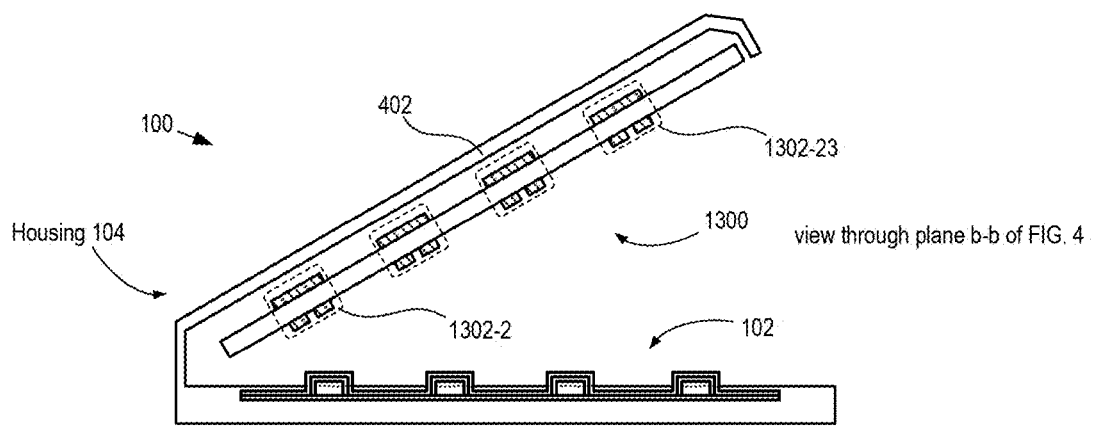
FIG. 13A depicts a schematic drawing of a cross-sectional view of package 100 having an alternative capacitive-sensing-based detection module.

FIG. 13A depicts a schematic drawing of a cross-sectional view of package 100 having an alternative capacitive-sensing-based detection module. Package 100 is depicted in its open state and with blister card 102 located in the package by receiver 106 (not shown for clarity). The package cross-section depicted in FIG. 13A is taken through a plane along line b-b depicted in FIG. 4.

Detection module 1300 includes sensor substrate 602 and sensors 1302-1 through 1302-28 (referred to, collectively, as sensors 1302), which are arranged on the substrate in an arrangement that matches that of tablets 210 on blister card 102.

Detection module 1300 is analogous to detection module 108 described above; however, detection module 1300 is located in lid 402 by a receiver that is analogous to receiver 106 described above (not shown for clarity). The closure of lid 402 brings detection module 1300 into close proximity with blister card 102, thereby operatively coupling each of sensors 1302 with its respective tablet 210.

Figure 13B:
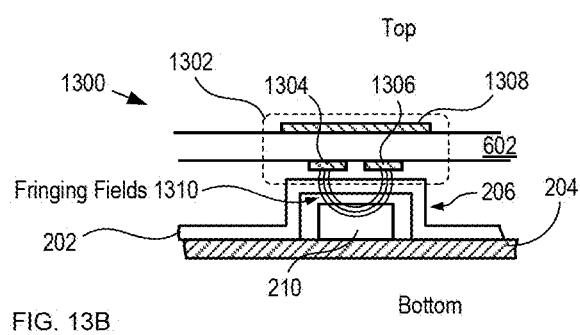
FIGS. 13B-C depict cross-sectional views a portion of detection module 1300 before and after dispensing of a tablet, respectively, in accordance with the present invention.
Figure 13C:
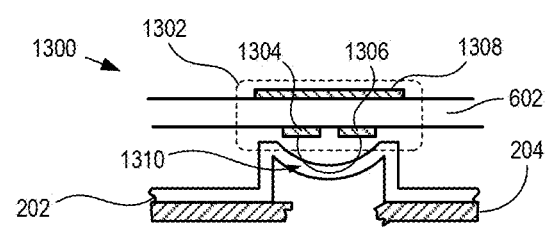

FIGS. 13B-C depict cross-sectional views a portion of detection module 1300 before and after dispensing of a tablet, respectively, in accordance with the present invention.

Each of sensors 1302 includes electrodes 1304 and 1306 and shield 1308.

Electrodes 1304 and 1306 are electrically conductive electrodes disposed on a first surface of substrate 602.

Shield 1308 is an electrically conductive electrode disposed on a second surface of substrate 602. Shield 1308 is grounded such that it is operative for shielding electrodes 1304 and 1306 from electrical noise and interference emanating from the top side of detection module 1300. Lidding film 204 is also typically grounded, thereby enabling it to act as a shield from the bottom side for electrodes 1304 and 1306.

When lid 402 is closed and tablet 210 is located in reservoir 206, electrodes 1304 and 1306 are capacitively coupled with tablet 210 via fringing fields 1310. As a result, the capacitance between electrodes 1304 and 1306 is based on these fringing fields.

When lid 402 is closed and reservoir 206 is empty of its tablet, however, fringing fields 1310 are coupled with only the remnants of reservoir 206 (i.e., deformed forming film 202), which gives rise to a difference in the capacitance between electrodes 1304 and 1306 from that of a filled reservoir because of the different manner in which fringing fields 1310 couple with the empty reservoir.

In operation, typically, detection module 1300 interrogates blister card 102 each time lid 402 is closed. The output signal from the detection module is then compared to the most recent previous blister-pack state to determine whether a tablet has been dispensed and, if so, which tablet. In some embodiments, the presence or absence of a tablet 210 in each reservoir 206 is determined by a change in the absolute magnitude of sense capacitances between lid closures, using a previously calibrated threshold value to indicate presence or absence of a tablet in each reservoir 206.

Figure 13D:
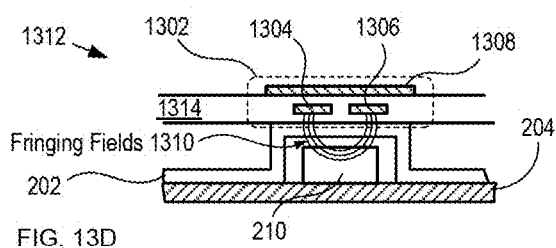
FIGS. 13D-E depict cross-sectional views of a portion of yet another alternative capacitive-sensing-based detection module, before and after dispensing of a tablet, respectively, in accordance with the present invention.
Figure 13E:
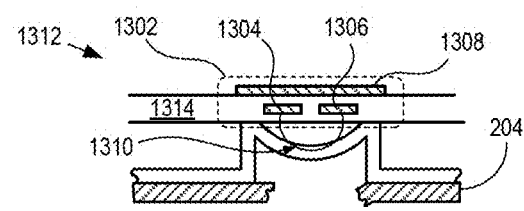

FIGS. 13D-E depict cross-sectional views of a portion of yet another alternative capacitive-sensing-based detection module, before and after dispensing of a tablet, respectively, in accordance with the present invention. Detection module 1312 is analogous to detection module 1300 described above; however, detection module 1312 is a flexible detection module that is dimensioned and arranged to be placed in contact with blister card 102 during operation.

Detection module 1312 includes substrate 1314 and the plurality of capacitive sensors 1302, as described above.

Substrate 1314 is a flexible substrate comprising polyimide. In some embodiments, substrate 1314 is formed of another material suitable for flexible electronics, such as a polymer, such as poly(methylacrylate) (PMMA), polyimide, polyurethane, polyester, polyether ether ketone (PEEK), and the like. Preferably, substrate 1314 is sufficiently flexible to enable a force applied to it to deform forming film 202 and push tablet 210 through lidding film 204.

When detection module 1312 is in contact with blister card 102, electrodes 1304 and 1306 are capacitively coupled with tablet 210 via fringing fields 1310. As discussed above, the capacitance between electrodes 1304 and 1306 is based on fringing fields 1310 such that the capacitance of each sensor 1302 is based on the presence of its respective tablet 210.

The use of a flexible substrate also enables integration of detection module 1312 in or on forming film 202.

In some embodiments of the present invention, detection module 1312 is formed such that it includes an interior volume for receiving blister card 102 (i.e., detection module has the form analogous to a flexible pouch). The interior volume is dimensioned and arranged such that, when blister card 102 is located in the pouch, the pouch holds the blister card in intimate contact on the top (forming-film side) and bottom surfaces (lidding-film side). The top and bottom surfaces of the pouch incorporate holes to enable access to reservoirs 206 and dispensing regions 212. Alternatively, as described in some embodiments above, the detection module may include a substrate that is sufficiently flexible to partially or fully cover the topside holes. It should be noted that such embodiments of the present invention can be implemented using more than one of the different sensing approaches described herein. These embodiments are particularly well suited for use with capacitive sensing and tactile sensing techniques.

Acoustic Sensing

Figure 14A:
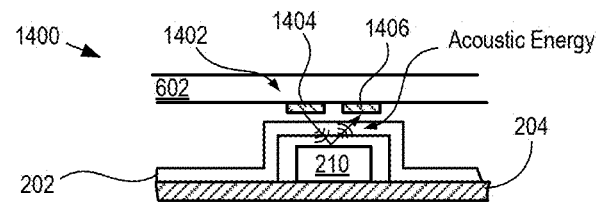
FIGS. 14A-B depict cross-sectional views of a portion an alternative acoustic-sensing-based detection module, before and after dispensing of a tablet, respectively, in accordance with the present invention.
Figure 14B:
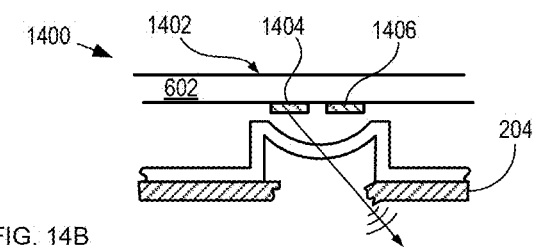

FIGS. 14A-B depict cross-sectional views of a portion an alternative acoustic-sensing-based detection module, before and after dispensing of a tablet, respectively, in accordance with the present invention. Detection module 1400 is analogous to detection module 108 described above; however, detection module 1400 includes substrate 602 and a plurality of acoustic sensors 1402, each of which is operative for detecting the presence of a tablet in a blister-card reservoir when the detection module is operatively coupled with a blister card from its forming-film side.

Each of acoustic sensors 1402 comprises transmitter 1404 and acoustic detector 1406.

Transmitter 1404 is a piezoelectric transducer operative as a conventional acoustic transmitter. Transmitter 1404 is arranged to direct acoustic energy (e.g., ultrasonic waves, etc.) toward tablet 210 when detection module 1400 is aligned with blister card 102.

Acoustic detector 1406 is a piezoelectric transducer operative as a conventional acoustic receiver. Acoustic detector 1406 is arranged to receive acoustic energy from the direction of tablet 210 when detection module 1400 is aligned with blister card 102.

In the depicted example, detection module 1400 is mounted on the inside surface of lid 402 of housing 104. Sensors 1402 are arranged on substrate 602 such that, when lid 402 is closed, the sensors are brought into contact with reservoirs 206 of blister card 102 to operatively couple each sensor with a different reservoir. In some embodiments, sensors 1402 and reservoirs 206 are separated by a small air gap when lid 402 is closed. In some embodiments, detection module 1400 is located within housing 104 via a receiver, as discussed above.

One skilled in the art will recognize, after reading this Specification, that the acoustic impedance of reservoir 206 is different when it is occupied with a tablet 210 versus when the reservoir is empty. In operation, each time lid 402 is closed, each of sensors 1402 provides an electrical signal whose magnitude is indicative of whether its respective reservoir contains a tablet. When a change in the acoustic impedance from the previous interrogation of blister card 102 is sensed, electronics module 110 can determine that a tablet-dispensing event has occurred, as well as identify which tablet has been dispensed. In some embodiments, the presence or absence of a tablet 210 in each reservoir 206 determined based on the absolute magnitude of acoustic signatures, using previously calibrated threshold values to indicate presence or absence of a tablet in each reservoir 206.

In some embodiments, detection module 1400 comprises a flexible substrate that is analogous to substrate 1312 described above. In such embodiments, sensors 1402 are formed in such substrate using flexible piezoelectric films (e.g., polyvinylidene fluoride or polyvinylidene difluoride, also known as PVDF, etc.) in accordance with conventional flexible-electronics fabrication technology. As discussed above, the use of a flexible substrate in detection module 1400 enables a force applied to the detection module to deform forming film 202 and push tablet 210 through lidding film 204. It also enables integration of detection module 1400 in or on forming film 202. Further, in some embodiments, a flexible substrate enables the use of the piezoelectric materials of sensors 1402 to harvest mechanical energy (e.g., such as that generated while a tablet is being dispensed) and convert it into electrical energy usable for powering detection module 1400.

One skilled in the art will recognize that detection module 1400 can be dimensioned and arranged for operation from the lidding film side of blister card 102 without departing from the scope of the present invention.

In some embodiments, transmitter-free acoustic sensing is achieved by disposing three or more microphones on blister card 102.

Figure 15:
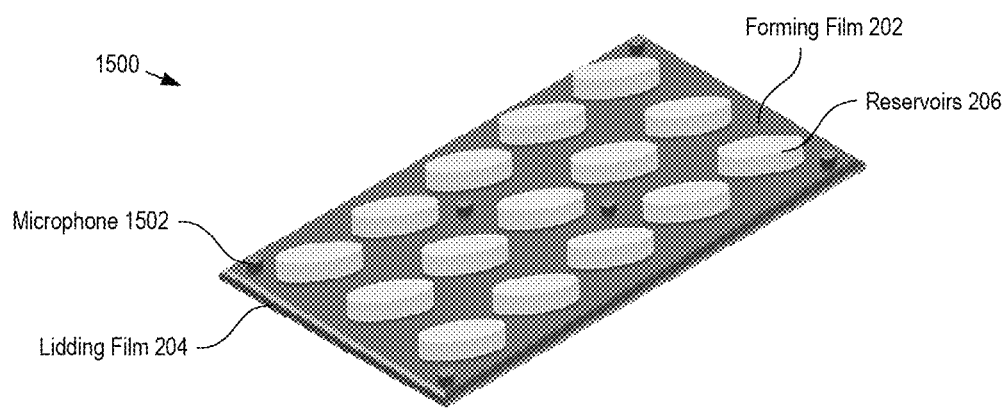
FIG. 15 depicts a schematic drawing of a perspective view of a blister card comprising a plurality of microphones in accordance with another acoustic-sensing-based embodiment of the present invention.

FIG. 15 depicts a schematic drawing of a perspective view of a blister card comprising a plurality of microphones in accordance with another acoustic-sensing-based embodiment of the present invention. Blister card 1500 is analogous to blister card 102; however, bister card 1500 includes six microphones 1502, which are disposed on forming film 202 and distributed across its area.

In operation, each microphone detects the sound of a tablet being dispensed. Signal processing capability included in electronics module 110 and/or mobile device 114 processes the outputs of the microphones to triangulate the sound and identify the specific tablet location at which it originates.

In some embodiments, detection module 1500 comprises a flexible substrate, which is placed in contact with blister card 102 within housing 104.

In some embodiments, detection module 1500 comprises a conventional PCB substrate that is mounted on the inside surface of lid 402 of housing 104.

In some embodiments, microphones 1502 are disposed on a PCB substrate having holes that enable force to be applied to reservoirs 206. For example, the PCB substrate would be in the shape of a frame, running along one or more of the inside sidewalls of the housing 104 adjacent to the blister card 102. In some embodiments, detection module 1500 is mounted therein. In some embodiments, detection module 1500 is located therein via a receiver.

Tactile Sensing

Figure 16A:
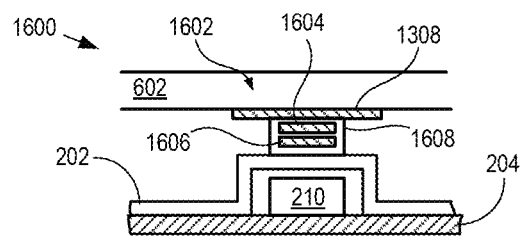
FIGS. 16A-B depict cross-sectional views of a portion a tactile-sensing-based detection module, before and after dispensing of a tablet, respectively, in accordance with the present invention.
Figure 16B:
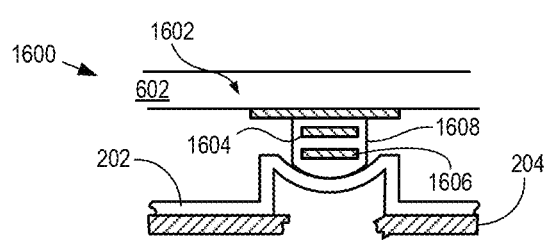

FIGS. 16A-B depict cross-sectional views of a portion of a tactile-sensing-based detection module, before and after dispensing of a tablet, respectively, in accordance with the present invention. Detection module 1600 is analogous to detection module 108 described above; however, detection module 1600 includes substrate 602 and a plurality of tactile sensors 1602, each of which is operative for detecting the presence of a tablet in a blister-card reservoir when detection module 1600 is operatively coupled with blister card 102 from its forming-film side. Sensors 1602 are disposed on substrate 602 in an arrangement that substantially matches the arrangement of tablets in blister card 102.

In the depicted example, detection module 1600 is mounted on the inside surface of the lid 402 of housing 104. In some embodiments, detection module 1600 is located within housing 104 via a receiver, as discussed above.

In the depicted example, each of tactile sensors 1602 includes electrodes 1604 and 1606 and optional shield 1308.

Each of tactile sensors 1602 is a parallel plate capacitor comprising conventional planar electrodes 1604 and 1606 and projection 1608, which is a projection of soft dielectric material (e.g., PMMA, etc.) disposed between and around electrodes 1604 and 1606. The capacitance of sensor 1602 is based on the spacing between its electrodes.

In operation, when lid 402 is closed, sensors 1602 are put into contact with reservoirs 206. When a tablet is contained in a reservoir, a pressure/force is generated between sensor 1602 and the reservoir, which is sufficient to depress the forming film 202 of the reservoir 206 but not large enough to break the lidding film 204 in the dispensing region 212.

This force causes compression of the material between electrodes 1604 and 1606, giving rise to a relatively large capacitance for sensor 1602. When a sensor is place in contact with a reservoir that does not contain a tablet, however, little, if any, force is generated between the sensor and the reservoir. As a result, the amount of compression of the material between electrodes 1604 and 1606 is minimal, giving rise to a relatively lower capacitance for the sensor.

At each closure of lid 402, therefore, electronics module 110 reads the capacitance of each sensor 1602 and determines which tablets have been dispensed from blister card 102.

In some embodiments, the region between electrodes 1604 and 1606 is occupied by a piezoelectric material, which provides an electrical output based on the force applied to tactile sensor 1602. Such embodiments allow for harvesting energy from the piezoelectric material to detect the state of the blister card 102 and power the detection module 1600.

In some embodiments, substrate 602 is replaced with a flexible substrate, such as substrate 1314. Typically, sensors 1602 are formed in such a substrate using flexible electronics fabrication technology. In such embodiments, detection module 1600 is sufficiently flexible to enable a force applied to it to deform forming film 202 to push tablet 210 through lidding film 204. Such embodiments enable integration of detection module 1600 in or on the forming film of the blister card.

In some embodiments, the detection module 1600 is operatively coupled with the blister card from its lidding-film side. Sensors 1602 are arranged between dispensing regions 212, such that they are operative for sensing forces imparted to bister card 104 during each dispensing operation.

It would be obvious to one skilled in the art, after reading this Specification, that there are a variety of ways to implement tactile sensing. For example, sensors 1602 can be realized based on any principle that generates a detectable signal, electrical or other, as a result of a tactile stimulus. A broader interpretation of tactile sensing would for example include measurement of deformations of the blister card 102 or surfaces of the housing 104 by utilizing strain sensors on/in flexible substrates directly printed on such surfaces.

Optical Sensing

Figure 17A:
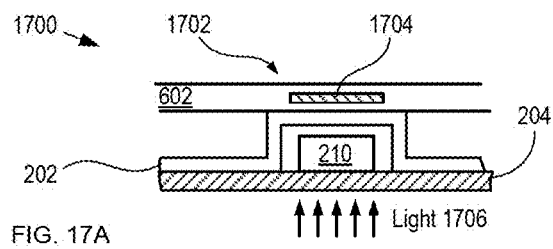
FIGS. 17A-B depict cross-sectional views of a portion an optical-sensing-based detection module, before and after dispensing of a tablet, respectively, in accordance with the present invention.
Figure 17B:
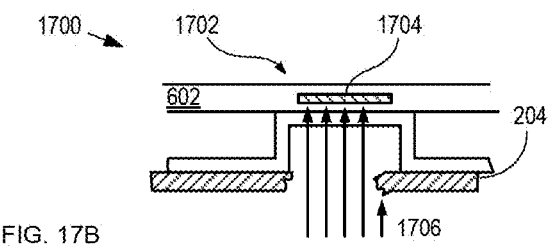

FIGS. 17A-B depict cross-sectional views of a portion of an optical-sensing-based detection module, before and after dispensing of a tablet, respectively, in accordance with the present invention. Detection module 1700 is analogous to detection module 108 described above; however, detection module 1700 includes substrate 602 and a plurality of optical sensors 1702, each of which is operative for detecting the presence of a tablet in a blister-card reservoir when the detection module is operatively coupled with a blister card from its forming-film side. In the depicted example, detection module 1700 is located on the inside surface of lid 402.

Each of sensors 1702 comprises photodetector 1704, which is operative for detecting light 1706. The plurality of photodetectors are disposed on substrate 602 in an arrangement that substantially matches that of tablets 210 of blister card 102.

In the depicted example, light 1706 is ambient light that originates outside housing 104. In some embodiments, light 1706 is provided by a light source included within package 100, typically mounted underneath detection module 108. Light sources in accordance with the present invention include, without limitation, diffuse light sources, arrays of light emitters (e.g., LEDs, lasers, etc.) aligned with photodetectors 1704, etc.

In operation, when a tablet 210 is dispensed, opaque lidding film 204 is fractured, thereby enabling light to pass through detection region 212 of that tablet site to reach photodetector 1704. As a result, detection of light by a photodetector signals that a tablet has been dispensed from its respective sensor location. In some embodiments, the state of blister card 102 is interrogated after each time lid 402 is closed.

Although detection module 1700 is disposed on the top side (i.e., forming-film side) of blister card 102 in the depicted example, it will be clear to one skilled in the art, after reading this Specification, how to make and use alternative embodiments of the present invention wherein detection module 1700 is disposed on the bottom side (i.e., lidding-film side) of blister card 102 such that light signal 1706 passes through the blister card from the top side to the bottom side. In some of these embodiments, the state of blister card 102 is determined at the opening of lid 402.

In some embodiments, the substrate of detection module 1700 is formed of a transparent, flexible substrate comprising a substantially transparent polymer, such as PMMA, polyimide, polyurethane, polyester, PEEK, and the like. In such embodiments, detection module 1700 can be located in contact with blister card 102. Preferably in such embodiments, the substrate is made of a material suitable for the formation of flexible electronics and is sufficiently flexible to enable a force applied to it to deform forming film 202 to push tablet 210 through lidding film 204. The use of a flexible substrate also enables integration of detection module 1700 in or on forming film 202.

In some embodiments, detection module 1700 includes planar-lightwave circuits (PLCs) whose surface waveguides convey light generated from a source remote to sensors 1702 to each sensor and collect light transmitted through the sensor region and convey it to a remote detector. Preferably, in such embodiments, the PLCs are substantially parallel with blister card 102 and light is coupled from the PLCs into and out of the sensor region via vertical grating couplers.

Figure 18A:
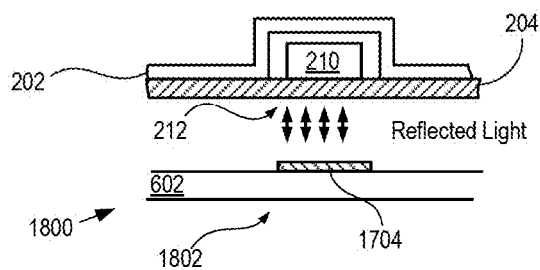
FIGS. 18A-B depict cross-sectional views of a portion an optical-sensing-based detection module, before and after dispensing of a tablet, respectively, in accordance with the present invention.
Figure 18B:
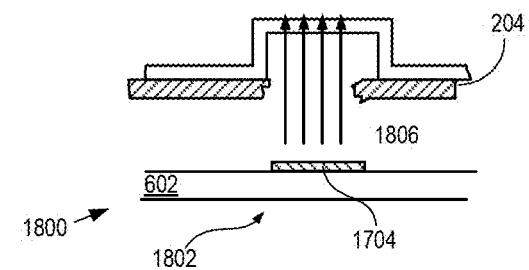

FIGS. 18A-B depict cross-sectional views of a portion of an optical-sensing-based detection module, before and after dispensing of a tablet, respectively, in accordance with the present invention. Detection module 1800 is analogous to detection module 1700 described above; however, detection module 1800 is located on the inside bottom surface of housing 104 and operates in reflection mode. Detection module 1800 includes a plurality of sensors 1802, which is arranged to match the arrangement of tablets in blister card 104.

Each sensor 1802 includes a photodiode 1704, which is dimensioned and arranged to detect light reflected from lidding film 204 only when its respective dispensing region 212 is intact. In the depicted example, sensors 1802 detect ambient light. In some embodiments, each of sensors 1802 also includes a light source for illuminating dispensing region 212. In some embodiments, a single light source is included in detection module 1800 to illuminate the entire lidding film with diffused light.

Thermal Sensing

As mentioned briefly above, thermal sensing can also be used to detect a tablet dispensing event in accordance with the present invention. By monitoring heat conduction across each dispensing region 212 of blister card 102, detection of the breaking of the lidding film in the dispensing region can be detected. In some embodiments, a first resistor disposed on lidding film 204 at one side of dispensing region 212 is driven to generate heat into the lidding film. The heat is then detected by a temperature sensor disposed on the lidding film 204 on the other side of the dispensing region. When the temperature of the heater is increased by an incremental amount, if the lidding film is intact in the dispensing region, a temperature rise is detected by the temperature sensor. When the lidding film is broken, however, heat conduction through dispensing region 212 is impeded and the detected temperature rise at the temperature sensor is significantly smaller.

It should be noted that the concepts of the present invention are applicable to smart packages suitable for monitoring the state of multiple blister packs.

Figure 19:
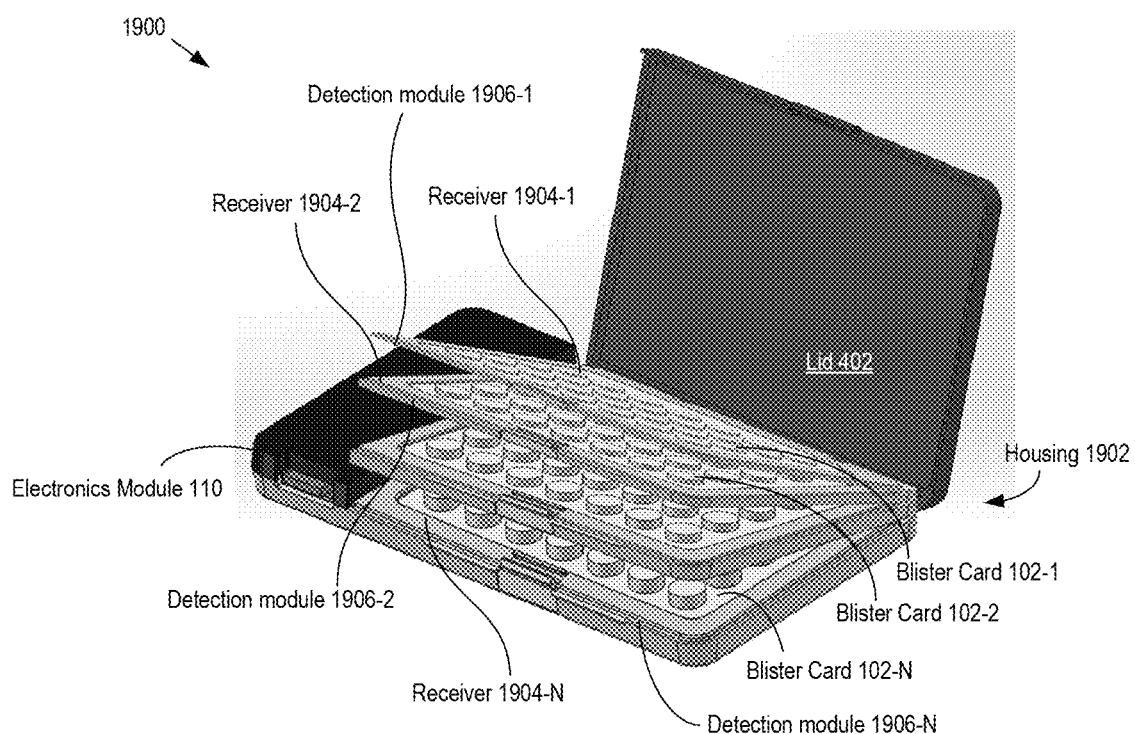
FIG. 19 depicts a schematic drawing of a perspective view of a multi-blister-card package in accordance with an alternative embodiment of the present invention.

FIG. 19 depicts a schematic drawing of a perspective view of a multi-blister-card package in accordance with an alternative embodiment of the present invention. Package 1900 is a metapackage that is operative for monitoring the state of multiple blister cards 102, where each blister card can have a different prescription or multiple copies of the same prescription.

Package 1900 includes housing 1902, electronics module 110, receivers 1904-1 through 1904-N and detection modules 1906-1 through 1906-N. Package 1900 is dimensioned and arranged to receive and locate blister cards 102-1 through 102-N.

Housing 1902 is analogous to housing 104; however, housing 1902 is dimensioned and arranged to contain multiple receivers, detection modules, and blister cards.

Each of receivers 1904-1 through 1904-N (referred to, collectively, as receivers 1904) is analogous to receiver 106; however, each receiver 1904 includes a hinge that enables it to be rotated out to expose a different blister card.

Each of detection modules 1906-1 through 1906-N (referred to, collectively, as detection modules 1906) is analogous to detection module 108; however, each detection module 1906 is dimensioned and arranged to monitor the status of a different blister card. In some embodiments, detection modules 108 employ multiple sensor technologies.

Each of detection modules 1906 is electrically coupled with electronics module 110 as described above, which enables operation of package 408 as described above and with respect to package 100.

It is to be understood that the disclosure teaches just some examples of embodiments of the present invention and that many variations of the invention can easily be devised by those skilled in the art after reading this disclosure and that the scope of the present invention is to be determined by the following claims.

What is claimed is:

1. A system for monitoring the state of at least one blister card that includes a forming film, a lidding film, and a first tablet contained in a first reservoir defined by the forming film and the lidding film, wherein the system comprises:
  a housing that is operative for locating the blister card in a first position;
  a first detection module comprising a first sensor that includes a first electrode and a second electrode, the first electrode and second electrode collectively defining a first capacitor having a first capacitance that is based on the physical state of a first dispensing region of the lidding film, wherein the first reservoir includes the first dispensing region, and wherein the first sensor is operative for providing a first electrical signal that is based on the first capacitance; and
  an electronics module that is operative for providing a first output signal based on the first electrical signal.

2. The system of claim 1 wherein a first electrode and the first dispensing region collectively define the first capacitor, and wherein the first capacitance has a first magnitude when the first dispensing region is intact and a second magnitude when the first dispensing region is broken, and wherein the first electrical signal is based on the first capacitance.

3. The system of claim 1 wherein the capacitance of the first capacitor is based on a fringing field between the dispensing region and the first electrode.

4. The system of claim 1 wherein the electronics module is operative for providing the first output signal as a wireless signal.

5. The system of claim 1 further comprising a tactile sensor that is operative for detecting a force applied to the blister card.

6. A system that is operative for monitoring the state of a first blister card that includes a first forming film, a first lidding film, and a first plurality of tablets that is arranged in a first arrangement, wherein each tablet of the first plurality thereof is contained in a different reservoir of a first plurality of reservoirs defined by the first forming film and first lidding film, and wherein the system comprises:
  a first detection module comprising a first plurality of sensors arranged in the first arrangement such that there is a one-to-one correspondence between the first plurality of sensors and the first plurality of reservoirs, wherein each sensor of the first plurality thereof includes a first electrode and a second electrode, the first electrode and second electrode collectively defining a capacitor whose capacitance is based on the physical state of a different dispensing region of a first plurality of dispensing regions of the first lidding film, and wherein each sensor is operative for providing an electrical signal of a first plurality thereof such that each electrical signal of the first plurality thereof is based on the capacitance of its capacitor; and
  an electronics module operative for providing a first output signal based on the first plurality of electrical signals.

7. The system of claim 6, wherein the system is further operative for monitoring the state of a second blister card, the second blister card including a second forming film, a second lidding film, and a second plurality of tablets that are arranged in a second arrangement, and wherein each tablet of the second plurality thereof is contained in a different reservoir of a second plurality of reservoirs defined by the second forming film and second lidding film, and further wherein the system further comprises:
  a second detection module comprising a second plurality of sensors arranged in the second arrangement, wherein each sensor of the second plurality thereof is operative for providing an electrical signal of a second plurality thereof such that each electrical signal of the second plurality thereof is based on the physical state of a different dispensing region of a second plurality of dispensing regions of the second lidding film;
  wherein the electronics module is further operative for providing a second output signal based on the second plurality of electrical signals.

8. The system of claim 6 further comprising a tactile sensor that is operative for detecting a force applied to the blister card.

9. The system of claim 6 wherein the first electrode of the capacitor of a first sensor of the first plurality thereof is capacitively coupled with a first dispensing region of the plurality thereof.

10. The system of claim 6 wherein the capacitor of a first sensor of the plurality thereof has a first capacitance that is based on a fringing field between the first electrode and a first dispensing region of the plurality thereof.

11. The system of claim 6 wherein the electronic module is operative for providing the first output signal as a wireless signal.

12. A method for monitoring the state of a blister card that includes a forming film, a lidding film, and a plurality of tablets that is arranged in a first arrangement, wherein each tablet of the plurality thereof is contained in a different reservoir of a plurality of reservoirs defined by the forming film and lidding film, wherein the method comprises:
- providing a detection module comprising a plurality of sensors that is arranged in the first arrangement such that there is a one-to-one correspondence between the plurality of sensors and the plurality of reservoirs, wherein each sensor of the plurality thereof includes a capacitor whose capacitance is based on the physical state of a different dispensing region of a plurality of dispensing regions of the lidding film, wherein each dispensing region of the plurality thereof is included in a different reservoir of the plurality of reservoirs;
- operatively coupling the plurality of sensors and the blister card such that each sensor of the plurality thereof is operative for providing an electrical signal based on the capacitance of its capacitor;
- determining a physical state of the blister card based on the plurality of electrical signals;
- comparing the physical state of the blister card with an expected state of the blister card, wherein the expected state is based on a predetermined prescription regimen for the plurality of tablets; and
- providing an output signal based on the physical state of the blister card relative to the expected state.

13. The method of claim 12 wherein the output signal is provided as a wireless signal.

14. The method of claim 12 further comprising monitoring the time and date, wherein the expected state is based on the monitored time and date.

15. The method of claim 12 further comprising initiating an error signal if the physical state and expected state are different.

16. The method of claim 12 wherein the detection module is provided such that the capacitance of each capacitor of the plurality thereof has a first magnitude when its respective dispensing region is intact and a second magnitude when its respective dispensing region is broken, and further wherein the output signal is based on the capacitance of at least one of the plurality of capacitors.

17. The method of claim 16 wherein each capacitor of the plurality thereof is defined by a first electrode and its respective dispensing region.

18. The method of claim 16 wherein each capacitor of the plurality thereof is defined by a first electrode and a second electrode, and wherein the capacitance of each capacitor is based on a fringing field between its respective dispensing region and its respective first electrode.

* * * * *